US012566140B2

(12) United States Patent
Gunn, III et al.

(10) Patent No.: US 12,566,140 B2
(45) Date of Patent: Mar. 3, 2026

(54) BIOSENSORS BASED ON OPTICAL PROBING AND SENSING

(71) Applicant: GENALYTE, INC., San Diego, CA (US)

(72) Inventors: Lawrence Cary Gunn, III, Encinitas, CA (US); Muzammil Iqbal, San Diego, CA (US); Brad Spaugh, San Diego, CA (US); Frank Tybor, Coronado, CA (US)

(73) Assignee: Genalyte, Inc., San Diego, CA (US)

( * ) Notice: Subject to any disclaimer, the term of this patent is extended or adjusted under 35 U.S.C. 154(b) by 1030 days.

(21) Appl. No.: 17/353,209

(22) Filed: Jun. 21, 2021

(65) Prior Publication Data

US 2022/0042920 A1 Feb. 10, 2022

Related U.S. Application Data

(63) Continuation of application No. 15/844,306, filed on Dec. 15, 2017, now Pat. No. 11,041,811, which is a (Continued)

(51) Int. Cl.
| | |
|---|---|
| *G01N 21/77* | (2006.01) |
| *G01N 21/25* | (2006.01) |
| *G01N 21/39* | (2006.01) |
| *G01N 33/543* | (2006.01) |
| *G02B 6/293* | (2006.01) |
| *G02B 6/34* | (2006.01) |
| *G01N 21/64* | (2006.01) |
| *G02B 6/12* | (2006.01) |

(52) U.S. Cl.
CPC ....... *G01N 21/7746* (2013.01); *G01N 21/255* (2013.01); *G01N 21/39* (2013.01); *G01N 21/774* (2013.01); *G01N 33/54373* (2013.01); *G01N 33/54393* (2013.01); *G02B 6/29338* (2013.01); *G02B 6/34* (2013.01); *G01N 21/648* (2013.01); *G02B 2006/12097* (2013.01); *G02B 2006/12138* (2013.01)

(58) Field of Classification Search
None
See application file for complete search history.

(56) References Cited

U.S. PATENT DOCUMENTS

| | | | |
|---|---|---|---|
| 4,078,052 | A | 3/1978 | Papahadjopoulos |
| 4,224,179 | A | 9/1980 | Schneider |

(Continued)

FOREIGN PATENT DOCUMENTS

| | | |
|---|---|---|
| CA | 2 355 816 | 6/2000 |
| CA | 2 555 962 | 9/2007 |

(Continued)

OTHER PUBLICATIONS

1994 Pierce Chemical Company Catalog, Technical Section on Cross-Linking, pp. 155-200.

(Continued)

*Primary Examiner* — Neil N Turk
(74) *Attorney, Agent, or Firm* — Brake Hughes Bellermann LLP

(57) ABSTRACT

Apparatus, sensor chips and techniques for optical sensing of substances by using optical sensors on sensor chips.

17 Claims, 13 Drawing Sheets

Related U.S. Application Data continuation of application No. 13/126,164, filed as application No. PCT/US2009/062268 on Oct. 27, 2009, now Pat. No. 9,846,126.

(60) Provisional application No. 61/108,862, filed on Oct. 27, 2008.

(56) References Cited

U.S. PATENT DOCUMENTS

| | | |
|---|---|---|
| 4,235,871 A | 11/1980 | Papahadjopoulos et al. |
| 4,308,166 A | 12/1981 | Marchetti et al. |
| 4,310,506 A | 1/1982 | Baldeschwieler et al. |
| 4,394,372 A | 7/1983 | Taylor |
| 4,474,893 A | 10/1984 | Reading |
| 4,485,054 A | 11/1984 | Mezei et al. |
| 4,508,703 A | 4/1985 | Redziniak et al. |
| 4,522,803 A | 6/1985 | Lenk et al. |
| 4,714,681 A | 12/1987 | Reading |
| 4,925,648 A | 5/1990 | Hansen et al. |
| 5,071,248 A | 12/1991 | Tiefenthaler et al. |
| 5,192,549 A | 3/1993 | Barenolz et al. |
| 5,270,163 A | 12/1993 | Gold et al. |
| 5,475,096 A | 12/1995 | Gold et al. |
| 5,478,755 A | 12/1995 | Attridge et al. |
| 5,539,082 A | 7/1996 | Nielsen et al. |
| 5,567,588 A | 10/1996 | Gold et al. |
| 5,573,920 A | 11/1996 | Randle |
| 5,595,877 A | 1/1997 | Gold et al. |
| 5,601,819 A | 2/1997 | Wong et al. |
| 5,637,459 A | 6/1997 | Burke et al. |
| 5,663,790 A * | 9/1997 | Ekstrom ............ G01N 21/7746 |
| | | 204/603 |
| 5,681,702 A | 10/1997 | Collins et al. |
| 5,683,867 A | 11/1997 | Biesecker et al. |
| 5,705,337 A | 1/1998 | Gold et al. |
| 5,714,331 A | 2/1998 | Buchardt et al. |
| 5,719,262 A | 2/1998 | Buchardt et al. |
| 5,939,021 A | 8/1999 | Hansen et al. |
| 6,043,060 A | 3/2000 | Imanishi |
| 6,210,891 B1 | 4/2001 | Nyren et al. |
| 6,268,490 B1 | 7/2001 | Imanishi et al. |
| 6,483,096 B1 | 11/2002 | Kunz et al. |
| 6,583,399 B1 | 6/2003 | Hunziker et al. |
| 6,657,731 B2 | 12/2003 | Tapalian et al. |
| 6,670,461 B1 | 12/2003 | Wengel et al. |
| 6,958,241 B2 | 10/2005 | Martin et al. |
| 7,083,920 B2 | 8/2006 | Werner et al. |
| 7,108,863 B2 | 9/2006 | Zalipsky et al. |
| 7,183,759 B1 | 2/2007 | Malendevish et al. |
| 7,208,174 B2 | 4/2007 | Huwyler et al. |
| 7,391,936 B2 | 6/2008 | Pau et al. |
| 7,528,403 B1 | 5/2009 | Borselli et al. |
| 7,778,499 B2 | 8/2010 | Janz et al. |
| 7,796,262 B1 | 9/2010 | Wang et al. |
| 9,366,635 B2 * | 6/2016 | Suh ........................ G01N 21/77 |
| 9,846,126 B2 | 12/2017 | Gunn, III et al. |
| 9,921,165 B2 | 3/2018 | Bailey et al. |
| 9,983,206 B2 | 5/2018 | Bailey et al. |
| 10,365,224 B2 | 7/2019 | Gunn, III |
| 10,739,340 B2 | 8/2020 | Bailey et al. |
| 11,041,811 B2 | 6/2021 | Gunn, III et al. |
| 2002/0012930 A1 | 1/2002 | Rothberg et al. |
| 2002/0037526 A1 | 3/2002 | Tashiro et al. |
| 2003/0017579 A1 | 1/2003 | Corn et al. |
| 2003/0027327 A1 | 2/2003 | Cunningham et al. |
| 2003/0027328 A1 | 2/2003 | Cunningham et al. |
| 2003/0039978 A1 | 2/2003 | Hannah |
| 2003/0096302 A1 | 5/2003 | Yguerabide et al. |
| 2003/0153023 A1 | 8/2003 | Starzl et al. |
| 2003/0207308 A1 | 11/2003 | Fulwyler et al. |
| 2003/0224370 A1 | 12/2003 | Rassman et al. |
| 2004/0023396 A1 | 2/2004 | Boyd et al. |
| 2004/0126875 A1 | 7/2004 | Putnam et al. |
| 2004/0145752 A1 | 7/2004 | Angeley |

| | | |
|---|---|---|
| 2004/0180362 A1 | 9/2004 | Lazar et al. |
| 2004/0191765 A1 | 9/2004 | Mozdy |
| 2004/0248318 A1 | 12/2004 | Weinberger et al. |
| 2005/0014179 A1 | 1/2005 | Karlsson et al. |
| 2005/0236589 A1 * | 10/2005 | Brunfeld ........... G01N 21/9501 |
| | | 250/559.11 |
| 2005/0250094 A1 | 11/2005 | Storhoff et al. |
| 2006/0063178 A1 | 3/2006 | Rauh-Adelmann et al. |
| 2006/0087656 A1 | 4/2006 | Barford |
| 2006/0119859 A1 | 6/2006 | Su et al. |
| 2006/0170931 A1 * | 8/2006 | Guo ................... G01N 21/7746 |
| | | 356/480 |
| 2006/0182659 A1 | 8/2006 | Unlu et al. |
| 2006/0194232 A1 | 8/2006 | Turner et al. |
| 2006/0215165 A1 | 9/2006 | Melman |
| 2006/0256350 A1 | 11/2006 | Nolte et al. |
| 2007/0081163 A1 | 4/2007 | Liang et al. |
| 2007/0147732 A1 | 6/2007 | Sanders |
| 2007/0195321 A1 | 8/2007 | Soussaline et al. |
| 2007/0237460 A1 | 10/2007 | Fan et al. |
| 2007/0241068 A1 | 10/2007 | Pamula et al. |
| 2008/0026394 A1 | 1/2008 | Labgold et al. |
| 2008/0038738 A1 | 2/2008 | Weigum et al. |
| 2008/0129997 A1 | 6/2008 | Yi et al. |
| 2008/0131939 A1 | 6/2008 | Roper |
| 2008/0138801 A1 | 6/2008 | He |
| 2008/0160622 A1 | 7/2008 | Su et al. |
| 2008/0181710 A1 | 7/2008 | Nakazawa et al. |
| 2008/0204760 A1 | 8/2008 | Gollier et al. |
| 2009/0046292 A1 | 2/2009 | Mirsky et al. |
| 2009/0170212 A1 | 7/2009 | Van Dijk et al. |
| 2009/0309049 A1 | 12/2009 | Van Dijk et al. |
| 2010/0009456 A1 | 1/2010 | Prins et al. |
| 2010/0105566 A1 | 4/2010 | Bieniarz et al. |
| 2010/0124787 A1 | 5/2010 | Nitkowski et al. |
| 2010/0165351 A1 | 7/2010 | Xu et al. |
| 2010/0297363 A1 | 11/2010 | Arnold et al. |
| 2011/0045472 A1 | 2/2011 | Gunn, III |
| 2011/0183363 A1 | 7/2011 | Fischer et al. |
| 2011/0275061 A1 | 11/2011 | Weidemaier et al. |
| 2012/0045748 A1 | 2/2012 | Willson et al. |
| 2013/0079599 A1 | 3/2013 | Holmes et al. |
| 2013/0157283 A1 | 6/2013 | Yung et al. |
| 2013/0157882 A1 | 6/2013 | Quan et al. |
| 2013/0189794 A1 | 7/2013 | Emeric et al. |
| 2013/0261010 A1 | 10/2013 | Bailey et al. |
| 2013/0295688 A1 | 11/2013 | Bailey et al. |
| 2013/0309135 A1 * | 11/2013 | Park ........................ G01N 21/17 |
| | | 422/69 |
| 2014/0070082 A1 | 3/2014 | Guo et al. |
| 2014/0273029 A1 | 9/2014 | Bailey et al. |
| 2015/0087551 A1 | 3/2015 | Halden |
| 2016/0017030 A1 | 1/2016 | Neu et al. |
| 2017/0176433 A1 | 6/2017 | Hauenstein et al. |
| 2018/0003706 A1 | 1/2018 | Trenholm et al. |
| 2018/0265861 A1 | 9/2018 | Chinnaiyan et al. |
| 2018/0299438 A1 | 10/2018 | Bailey et al. |
| 2019/0003975 A1 | 1/2019 | Bailey et al. |
| 2019/0170631 A1 | 6/2019 | Shachar et al. |
| 2020/0096451 A1 | 3/2020 | Gunn, III et al. |
| 2021/0140955 A1 | 5/2021 | Bailey et al. |
| 2021/0231651 A1 | 7/2021 | Brown et al. |

FOREIGN PATENT DOCUMENTS

| | | |
|---|---|---|
| DE | 10 2016 212 844 | 1/2018 |
| EP | 0 740 156 | 10/1996 |
| EP | 2 347 247 | 7/2011 |
| EP | 2 635 710 | 9/2013 |
| EP | 2 825 885 | 1/2015 |
| FR | 2 784 189 | 4/2000 |
| JP | 01-287427 | 11/1989 |
| JP | 02-297497 | 12/1990 |
| JP | 04-169257 | 6/1992 |
| JP | 2924707 | 7/1999 |
| JP | 2002-526773 | 8/2002 |
| JP | 2004-354068 | 12/2004 |
| JP | 2004-361087 | 12/2004 |
| JP | 2005-140683 | 6/2005 |

(56)                  References Cited

FOREIGN PATENT DOCUMENTS

| | | |
|---|---|---|
| JP | 2005-321244 | 11/2005 |
| JP | 2006-029883 | 2/2006 |
| JP | 2006-153643 | 6/2006 |
| JP | 2006-234810 | 9/2006 |
| JP | 2006-267052 | 10/2006 |
| JP | 2007-220864 | 8/2007 |
| JP | 2007-309886 | 11/2007 |
| JP | 2008-057997 | 3/2008 |
| JP | 2010-511864 | 4/2010 |
| JP | 2010-518394 | 5/2010 |
| JP | 2012-507035 | 3/2012 |
| JP | 5656853 | 12/2014 |
| WO | WO 91/000360 | 1/1991 |
| WO | WO 92/000509 | 1/1992 |
| WO | WO 92/005793 | 4/1992 |
| WO | WO 92/008802 | 5/1992 |
| WO | WO 93/017715 | 9/1993 |
| WO | WO 98/039352 | 9/1998 |
| WO | WO 99/014226 | 3/1999 |
| WO | WO 00/020861 | 4/2000 |
| WO | WO 00/056746 | 9/2000 |
| WO | WO 00/056748 | 9/2000 |
| WO | WO 00/066604 | 11/2000 |
| WO | WO 01/000641 | 1/2001 |
| WO | WO 01/001455 | 1/2001 |
| WO | WO 01/007455 | 2/2001 |
| WO | WO 03/052097 | 6/2003 |
| WO | WO 2004/109284 | 12/2004 |
| WO | WO 2005/066612 | 7/2005 |
| WO | WO 2005/080602 | 9/2005 |
| WO | WO 2005/090947 | 9/2005 |
| WO | WO 2005/118871 | 12/2005 |
| WO | WO 2007/033385 | 3/2007 |
| WO | WO 2007/081163 | 7/2007 |
| WO | WO 2008/054170 | 5/2008 |
| WO | WO 2008/070437 | 6/2008 |
| WO | WO 2008/081719 | 7/2008 |
| WO | WO 2008/097199 | 8/2008 |
| WO | WO 2009/069009 | 6/2009 |
| WO | WO 2009/075473 | 6/2009 |
| WO | WO 2009/076323 | 6/2009 |
| WO | WO 2010/062627 | 6/2010 |
| WO | WO 2011/091037 | 7/2011 |
| WO | WO 2012/061778 | 5/2012 |
| WO | WO 2013/138251 | 9/2013 |
| WO | WO 2014/143637 | 9/2014 |

OTHER PUBLICATIONS

Agnew et al., "Iterative In Situ Click Chemistry Creates Antibody-like Protein-Capture Agents", Angewandte Chemie International Edition in English, 2009, vol. 48, No. 27, pp. 4944-4948.

Allen et al., "Nuclear Factor-KB-Related Serum Factors as Longitudinal Biomarkers of Response and Survival in Advanced Oropharyngeal Carcinoma", Clinical Cancer Research, 2007, vol. 13, pp. 3182-3190.

Alvarez-Garcia et al., "MicroRNA Functions in Animal Development and Human Disease", Development, 2005, vol. 132, No. 21, pp. 4653-4662.

Ambros et al., "A Uniform System for MicroRNA Annotation", RNA, 2003, vol. 9, pp. 277-279.

Anderson et al., "The Human Plasma Proteome: History, Character, and Diagnostic Prospects", Molecular & Cellular Proteomics, 2002, vol. 1, No. 11, pp. 845-867.

Angelopoulos et al., "Cytokines in Alzheimer's Disease and Vascular Dementia", International Journal of Neuroscience, 2008, vol. 118, No. 12, pp. 1659-1672.

Anoop et al., "CSF Biomarkers for Alzheimer's Disease Diagnosis", International Journal of Alzheimer's Disease, 2010, pp. 1-12.

Arima et al., "Surface Plasmon Resonance and Surface Plasmon Field-Enhanced Fluorescence Spectroscopy for Sensitive Detection of Tumor Markers", Biosensors and Biodetection, 2009, pp. 3-20.

Armani et al., "Label-Free, Single-Molecule Detection with Optical Microcavities", Science, Aug. 10, 2007, vol. 317, pp. 783-787.

Arnold et al., "Shift of Whispering-Gallery Modes in Microspheres by Protein Adsorption", Optics Letters, Feb. 15, 2003, vol. 28, No. 4, pp. 272-274.

Arnold et al., "Whispering Gallery Mode Bio-Sensor for Label-Free Detection of Single Molecules: Thermos-Optic vs. Reactive Mechanism", Optics Express, Jan. 4, 2010, vol. 18, No. 1, pp. 281-287.

Azevedo et al., "Stability of Free and Immobilised Peroxidase in Aqueous-Organic Solvents Mixtures", Journal of Molecular Catalysis B: Enzymatic, Nov. 2001, vol. 15, pp. 147-153.

Babak et al., "Probing MicroRNAs with Microarrays: Tissue Specificity and Functional Inference", RNA, 2004, vol. 10, pp. 1813-1819.

Bachhawat-Sikder et al., "Mixed-Element Capture Agents: A Simple Strategy for the Construction of Synthetic, High-Affinity Protein Capture Ligands", Journal of the Amercian Chemistry Society, 2003, vol. 125, pp. 9550-9551.

Bailey et al., "A Robust Silicon Photonic Platform for Multiparameter Biological Analysis", Proceedings of SPIE: Silicon Photonics IV, The International Society for Optical Engineering, San Jose, CA, 2009, vol. 7220, pp. 72200N-1-6.

Bailey et al., "DNA-Encoded Antibody Libraries: A Unified Platform for Multiplexed Cell Sorting and Detection of Genes and Proteins", Journal of the American Chemical Society, Feb. 21, 2007, vol. 129, No. 7, pp. 1959-1967.

Bailey et al., "Large-Scale Resonance Amplification of Optical Sensing of Volatile Compounds with Chemoresponsive Visible-Region Diffraction Gratings", Journal of the American Chemical Society, 2002, vol. 124, pp. 6767-6774.

Bailey et al., "Real-Time Multicolor DNA Detection with Chemoresponsive Diffraction Gratings and Nanoparticle Probes", Journal of the American Chemical Society, 2003, vol. 125, No. 44, pp. 13541-13547.

Bailey et al., "Sensing via Optical Interference", Materials Today, Apr. 2005, vol. 8, pp. 46-52.

Baker et al., "Plasma and Cerebrospinal Fluid Interleukin-6 Concentrations in Posttraumatic Stress Disorder", NeuroImmunoModulation, 2001, vol. 9, No. 4, pp. 209-217.

Barrios et al., "Label-Free Optical Biosensing With Slot-Waveguides", Optics Letters, Apr. 1, 2008, vol. 33, No. 7, pp. 708-710.

Bartel et al., "MicroRNAs: At the Root of Plant Development?" Plant Physiology, Jun. 2003, vol. 132, pp. 709-717.

Bartel, David P., "MicroRNAs: Genomics, Biogenesis, Mechanism, and Function", Cell, Jan. 23, 2004, vol. 116, pp. 281-297.

Bayley et al., "Resistive-Pulse Sensing—From Microbes to Molecules", Chemical Reviews, 2000, vol. 100, pp. 2575-2594.

Bayley et al., "Stochastic Sensors Inspired by Biology", Nature, Sep. 13, 2001, vol. 413, pp. 226-230.

Bell et al., "Interleukin-6 and Interleukin-10 in Cerebrospinal Fluid after Severe Traumatic Brain Injury in Children", Journal of Neurotrauma, 1997, vol. 14, No. 7, pp. 451-457.

Berezovski et al., "Affinity Analysis of a Protein-Aptamer Complex Using Nonequilibrium Capillary Electrophoresis of Equilibrium Mixtures", Analytical Chemistry, 2003, vol. 75, pp. 1382-1386.

Berry et al., "One-Step Purification of Nucleic Acid for Gene Expression Analysis via Immiscible Filtration Assisted by Surface Tension (IFAST)", Lab Chip, 2011, vol. 11, pp. 1747-1753.

Bienstman et al., "Silicon Nanophotonics Using Deep-UV Lithography", SPIE, PO Box 10 Bellingham WA, 98227-0010 USA, vol. 6351, 2006.

Black et al., "C-Reactive Protein", The Journal of Biological Chemistry, vol. 279, No. 47, Nov. 19, 2004, pp. 48487-48490.

Blennow et al., "Cerebrospinal Fluid and Plasma Biomarkers in Alzheimer Disease", Nature Reviews: Neurology, Mar. 2010, vol. 6, No. 3, pp. 131-144.

Blicharz et al., "Fiber-Optic Microsphere-Based Antibody Array for the Analysis of Inflammatory Cytokines in Saliva", Analytical Chemistry, Mar. 15, 2009, vol. 81, No. 6, pp. 2106-2114.

Blum-Degen et al., "Interleukin-1B and Interleukin-6 are Elevated in the Cerebrospinal Fluid of Alzheimer's and De Novo Parkinson's Disease Patients", Neuroscience Letters, 1995, vol. 202, pp. 17-20.

(56)        References Cited

OTHER PUBLICATIONS

Boguslawski et al., "Characterization of Monoclonal Antibody to DNA-RNA and its Application to Immunodetection of Hybrids", Journal of Immunological Methods, 1986, vol. 89, pp. 123-130.

Boozer et al., "Looking Towards Label-Free Biomolecular Interaction Analysis in a High-Throughput Format: A Review of New Surface Plasmon Resonance Technologies", Current Opinion in Biotechnology, 2006, vol. 17, pp. 400-405.

Born et al., "Principles of Optics: Electromagnetic Theory of Propagation, Interference and Diffraction of Light", Sixth Edition, 1980, pp. 808, [Uploaded in 2 parts].

Braasch et al., "Locked Nucleic Acid (LNA): Fine-Tuning the Recognition of DNA and RNA", Chemistry & Biology, vol. 8, No. 1, pp. 1-7.

Braasch et al., "Novel Antisense and Peptide Nucleic Acid Strategies for Controlling Gene Expression", Biochemistry, Apr. 9, 2002, vol. 41, No. 14, pp. 4503-4510.

Brody et al., "Aptamers as Therapeutic and Diagnostic Agents", Reviews in Molecular Biotechnology, 2000, vol. 74, pp. 5-13.

Bustamante et al., "Grabbing the Cat by the Tail: Manipulating Molecules One by One", Nature Reviews Molecular Cell Biology, 2000, vol. 1, pp. 130-136.

Byeon et al., "Efficient Bioconjugation of Protein Capture Agents to Biosensor Surfaces Using Aniline-Catalyzed Hydrazone Ligation", Langmuir, Oct. 5, 2010, vol. 26, No. 19, pp. 15430-15435.

Byeon et al., "Multiplexed Evaluation of Capture Agent Binding Kinetics Using Arrays of Silicon Photonic Microring Resonators", Analyst, Sep. 7, 2011, vol. 136, No. 17, pp. 3430-3433.

Calin et al., "MicroRNA-Cancer Connection: The Beginning of a New Tale", Cancer Research, Aug. 1, 2006, vol. 66, No. 15, pp. 7390-7394.

Cao et al., "Optical Absorption and Structural Studies of Erbium Biphthalocyanine Sublimed Films", Materials Letters, 2003, vol. 57, pp. 4309-4314.

Capule et al., "An ELISA-Based Method to Quantify the Association of Small Molecules with Aggregated Amyloid Peptides", Analytical Chemistry, Feb. 7, 2012, vol. 84, No. 3, pp. 1786-1791.

Casebolt et al., "Monoclonal Antibody Solution Hybridization Assay for Detection of Mouse Hepatitis Virus Infection", Journal of Clinical Microbiology, Mar. 1992, vol. 30, No. 3, pp. 608-612.

Chan et al., "MicroRNA-21 is an Antiapoptotic Factor in Human Glioblastoma Cells", Cancer Research, Jul. 15, 2005, vol. 65, No. 14, pp. 6029-6033.

Chao et al., "Biochemical Sensors Based on Polymer Microrings with Sharp Asymmetrical Resonances", Applied Physics Letters, Aug. 25, 2003, vol. 83, No. 8, pp. 1527-1529.

Chao et al., "Polymer Microring Resonators for Biochemical Sensing Applications", IEEE Journal of Selected Topics in Quantum Electronics, Jan./Feb. 2006, vol. 12, No. 1, pp. 134-142.

Chavey et al., "Oestrogen Receptor Negative Breast Cancers Exhibit High Cytokine Content", Breast Cancer Research, Jan. 29, 2007, vol. 9, No. 1, pp. 1-11.

Chen et al., "Facile Synthesis of Gold-Silver Nanocages with Controllable Pores on the Surface", Journal of American Chemical Society, Nov. 22, 2006, vol. 128, No. 46, pp. 14776-14777.

Chen et al., "Gold Nanocages: Bioconjugation and Their Potential Use as Optical Imaging Contrast Agents", Nano Letters, 2005, vol. 5, No. 3, pp. 473-477.

Chen et al., "Immuno Gold Nanocages with Tailored Optical Properties for Targeted Photothermal Destruction of Cancer Cells", Nano Letters, May 2007, vol. 7, No. 5, pp. 1318-1322.

Chen et al., "MicroRNAs Modulate Hematopoietic Lineage Differentiation", Science, Jan. 2, 2004, vol. 303, pp. 83-86.

Chen et al., "Plasmon-Enhanced Colorimetric ELISA with Single Molecule Sensitivity", Nano Letters, 2011, vol. 11, No. 4, pp. 1826-1830.

Chen et al., "Real-Time Quantification of MicroRNAs by Stem-Loop RT-PCR", Nucleic Acids Research, 2005, vol. 33, No. 20, pp. 9.

Choi et al., "Immuno-Hybridization Chain Reaction for Enhancing Detection of Individual Cytokine-Secreting Human Peripheral Mononuclear Cells", Analytical Chemistry, Sep. 1, 2011, vol. 83, No. 17, pp. 6890-6895.

Clark et al., "Characteristics of the microplate method of enzyme-linked immunosorbent assay for the detection of plant viruses," J. Gen. Virol., 34: 475-483, (1977).

Conyers et al., "Chromogenic Substrates for Horseradish Peroxidase", Analytical Biochemistry, 1991, vol. 192, pp. 207-211.

Coutlée et al., "Immunodetection of DNA with Biotinylated RNA Probes: A Study of Reactivity of a Monoclonal Antibody to DNA-RNA Hybrids", Analytical Biochemistry, 1989, vol. 181, No. 1, pp. 96-105.

Dammer et al., "Specific Antigen/Antibody Interactions Measured by Force Microscopy", Biophysical Journal, vol. 0 70, May 1996, pp. 2437-2441.

De Vos et al., "SOI Optical Microring Resonator with Poly(ethylene glycol) Polymer Brush for Label-Free Biosensor Applications", Biosensors and Bioelectronics, Apr. 15, 2009, vol. 24, No. 8, pp. 2528-2533.

Dirks et al., "Triggered Amplification by Hybridization Chain Reaction", Proceedings of the National Academy of Sciences of the United States of America (PNAS), Oct. 26, 2004, vol. 101, No. 43, pp. 15275-15278.

Dirksen et al., "Rapid Oxime and Hydrazone Ligations with Aromatic Aldehydes for Biomolecular Labeling", Bioconjugate Chemistry, Dec. 2008, vol. 19, No. 12, pp. 2543-2548.

Dobbs et al., "Caution! Piranha solutions are extraordinarily dangerous, reacting explosively with trace quantities of organics", Chemical & Engineering News, Apr. 23, 1990, p. 2.

Durand et al., "A 275 Basepair Fragment at the 5' End of the Interleukin 2 Gene Enhances Expression from a Heterologous Promoter in Response to Signals from the T Cell Antigen Receptor", Journal of Experimental Medicine, Feb. 1987, vol. 165, pp. 395-407.

Eddowes, M.J., "Direct Immunochemical Sensing: Basic Chemical Principles and Fundamental Limitations", Biosensors, 1987, vol. 3, pp. 1-15.

Elayadi et al., "Application of PNA and LNA Oligomers to Chemotherapy", Current Opinion in Investigational Drugs, 2001, vol. 2, No. 4, pp. 558-561.

Elia et al., "Affinity-Capture Reagents for Protein Arrays", Trends in Biotechnology, 2002, vol. 20, No. 12, pp. S19-S22.

Ellington et al., "In Vitro Selection of RNA Molecules that Bind Specific Ligands", Nature, Aug. 30, 1990, vol. 346, pp. 818-822.

Ellison et al., "Standard Additions: Myth and Reality", Analyst, 2008, vol. 133, pp. 992-997.

Engelborghs et al., "Unchanged Levels of Interleukins, Neopterin, Interferon-γ and Tumor Necrosis Factor-α in Cerebrospinal Fluid of Patients with Dementia of the Alzheimer Type", Neurochemistry International, 1999, vol. 34, pp. 523-530.

Engvall et al., "Enzyme-Linked Immunosorbent Assay (ELISA) Quantitative Assay for Immunoglobulin G", Immunochemistry, 1971, vol. 8, pp. 871-874.

"EnzMet™—Enzyme Metallography", Nanoprobes.com Inc., <http://www.nanoprobes.com/products/EnzMet-SISH-enzyme-metallography-for-ISH-and-IHC.html>, printed Jun. 16, 2017 in 4 pages.

"EnzMet™ HRP Detection Kit for IHC / ISH", Nanoprobes Inc., Yaphank, NY, Jan. 2008, pp. 5.

Enzyme Linked Immunosorbent Assay (ELISA), eBioscience, 2010, pp. 8. <http://www.ebioscience.com/media/pdf/best-protocols/enzyme-linked-immunosorbent-assay-elisa.pdf>.

Erlanson et al., "In Situ Assembly of Enzyme Inhibitors Using Extended Tethering", Nature Biotechnology, Mar. 2003, vol. 21, pp. 308-314.

Evanko, Daniel, "Hybridization Chain Reaction", Nature Methods, Dec. 2004, vol. 1, No. 3, pp. 186-187.

Fagan et al., "Cerebrospinal Fluid Biomarkers of Alzheimer's Disease", Biomarkers in Medicine, Feb. 2010, vol. 4, No. 1, pp. 51-63.

Fan et al., "Sensitive Optical Biosensors for Unlabeled Targets: a Review", Analytica Chimica Acta, Jul. 14, 2008, vol. 620, No. 1-2, pp. 8-26.

(56)          References Cited

OTHER PUBLICATIONS

Fang et al., "Attomole Microarray Detection of microRNAs by Nanoparticle-Amplified SPR Imaging Measurements of Surface Polyadenylation Reactions", Journal of the American Chemical Society, Nov. 1, 2006, vol. 128, No. 43, pp. 14044-14046.

Fang et al., "Detection of Chemical Species Using Ultraviolet Microdisk Lasers", Applied Physics Letters, Oct. 25, 2004, vol. 85, No. 17, pp. 3666-3668.

Fineberg et al., "MicroRNAs Potentiate Neural Development", Neuron, Nov. 12, 2009, vol. 64, No. 3, pp. 303-309.

Fliss et al., "Anti-DNA • RNA Antibodies: An Efficient Tool for Non-Isotopic Detection of Listeria Species Through a Liquid-Phase Hybridization Assay", Applied Microbiology and Biotechnology, 1995, vol. 43, pp. 717-724.

Fortin et al., "Imaging of DNA Hybridization on Microscopic Polypyrrole Patterns Using Scanning Electrochemical Microscopy (SECM): the HRP Bio-Catalyzed Oxidation of 4-Chloro-1-Naphthol", Analyst, 2006, vol. 131, pp. 186-193.

Friedman et al., "Most Mammalian mRNAs are Conserved Targets of MicroRNAs", Genome Research, Jan. 2009, vol. 19, No. 1, pp. 92-105.

Frisk et al., "Synaptotagmin II Peptide-Bead Conjugate for Botulinum Toxin Enrichment and Detection in Microchannels", Biosensors and Bioelectronics, 2011, vol. 26, pp. 1929-1935.

Fujita et al., "Cytokine Profiling of Prostatic Fluid from Cancerous Prostate Glands", Prostate, Jun. 1, 2008, vol. 68, No. 8, pp. 872-882.

Gabay, Cem, "Interleukin-6 and Chronic Inflammation", Arthritis Research & Therapy, 2006, vol. 8, No. 2, S3, pp. 6.

Gangaraju et al., "MicroRNAs: Key Regulators of Stem Cells", Nature Reviews Molecular Cell Biology, Feb. 2009, vol. 10, No. 2, pp. 116-125.

Gauldie et al., "Interferon B2/B-cell Stimulatory Factor Type 2 Shares Identity with Monocyte-Derived Hepatocyte-Stimulating Factor and Regulates the Major Acute Phase Protein Response in Liver Cells", Proceedings of the National Academy of Sciences of the United States of America (PNAS), Oct. 1987, vol. 84, pp. 7251-7255.

Ge et al., "Molecularly Imprinted Sorbent Assays: Recent Developments and Applications", Chemistry: A European Journal, 2009, vol. 15, pp. 8100-8107.

Gebert et al., "*Helicobacter pylori* Vacuolating Cytotoxin Inhibits T Lymphocyte Activation", Science, Aug. 22, 2003, vol. 301, pp. 1099-1102.

Giesler et al., "Bean Pod Mottle Virus: A Threat to U.S. Soybean Production", Plant Disease, 2002, vol. 86, No. 12, pp. 1280-1289.

Gijs et al., "Microfluidic Application of Magentic Particles for Biological Analysis and Catalysis", Chemical Review, 2010, vol. 110, pp. 1518-1563.

Goodman, Joseph W., "Introduction to Fourier Optics", 3rd Edition, 2004, pp. 491.

Gorris et al., "Mechanistic Aspects of Horseradish Peroxidase Elucidated through Single-Molecule Studies", Journal of the American Chemical Society, 2009, vol. 131, No. 17, pp. 6277-6282.

Gullberg et al., "A Sense of Closeness: Protein Detection by Proximity Ligation", Current Opinion in Biotechnology, 2003, vol. 14, pp. 82-86.

Gusev et al., "Rolling Circle Amplification: A New Approach to Increase Sensitivity for Immunohistochemistry and Flow Cytometry", The American Journal of Pathology, Jul. 2001, vol. 159, pp. 63-69.

Haddadpour et al., "Metallic Nanoparticle on Micro Ring Resonator for Bio Optical Detection and Sensing", Biomedical Optics Express, Sep. 1, 2010, vol. 1, No. 2, pp. 378-384.

Hansson et al., "Association Between CSF Biomarkers and Incipient Alzheimer's Disease in Patients with Mild Cognitive Impairment: A Follow-Up Study", The Lancet Neurology, 2006, vol. 5, No. 3, pp. 228-234.

Hao et al., Synthesis and Optical Properties of 'Branched' Gold Nanocrystals, Nano Letters, 2004, vol. 4, No. 2, pp. 327-330.

Hao et al., "The Optical Properties of Metal Nanoshells", Journal of Physical Chemistry B, 2004, vol. 108, pp. 1224-1229.

Heath et al., "Nanotechnology and Cancer," Annual Review of Medicine, 2008, vol. 59, pp. 251-265.

Hecht, Eugene, "Optics", 4th Edition, Adelphi Univesity, Addison-Wesley, 2002, pp. 698. [Uploaded in 2 parts].

Heyduk et al., "Molecular Pincers: New Antibody-Based Homogeneous Protein Sensors", Analytical Chemistry, Jul. 1, 2008, vol. 80, No. 13, pp. 5152-5159.

Ho et al., "DNA as a Force Sensor in an Aptamer-Based Biochip for Adenosine", Analytical Chemistry, 2009, vol. 81, pp. 3159-3164.

Homola et al., "Surface Plasmon Resonance Sensors for Detection of Chemical and Biological Species", Chemical Review, 2008, vol. 108, pp. 462-493.

Homola et al., "Surface Plasmon Resonance Sensors: Review", Sensors and Actuators B, 1999, vol. 54, pp. 3-15.

Hornstein et al., "The MicroRNA miR-196 acts Upstream of Hoxb8 and Shh in Limb Development", Nature, Dec. 1, 2005, vol. 438, pp. 671-674.

Horowitz et al., "The Art of Electronics", 2nd Edition, Cambridge University Press, 1989, pp. 1125. [Uploaded in 4 Parts].

Hosoda et al., "A Comparison of Chromogenic Substrates for Horseradish Peroxidase as a Label in Steroid Enzyme Immunoassay", Chemical and Pharmaceutical Bulletin, 1986, vol. 34, No. 10, pp. 4177-4182.

Hu et al., "An Antibody-Based Microarray Assay for Small RNA Detection", Nucleic Acids Research, 2006, vol. 34, No. 7, e52, pp. 7.

Huell et al., "Interleukin-6 is Present in Early Stages of Plaque Formation and is Restricted to the Brains of Alzheimer's Disease Patients", Acta Neuropathologica, 1995, vol. 89, No. 6, pp. 544-551.

Hutvagner et al., "A Cellular Function for the RNA-Interference Enzyme Dicer in the Maturation of the let-7 Small Temporal RNA", Science, Aug. 3, 2001, vol. 293, pp. 834-838.

Ihenetu et al., "Pharmacological Characterisation of Cannabinoid Receptors Inhibiting Interleukin 2 Release from Human Peripheral Blood Mononuclear Cells", European Journal of Pharmacology, 2003, vol. 464, pp. 207-215.

Invitrogen, "Fetal Bovine Serum—Qualified", Invitrogen Cat# 26140, 2009, pp. 6, <http://tools.invitrogen.com/content/sfs/productnotes/F_FBS%20Qualified%20RD-MKT-TL-HL0506021.pdf>.

Iqbal et al., "Label-Free Biosensor Arrays Based on Silicon Ring Resonators and High-Speed Optical Scanning Instrumentation", IEEE Journal of Secelcted Topics in Quantum Electronics, May/Jun. 2010, vol. 16, No. 3, pp. 654-661.

Ivanov et al., "Chip-Based Nanostructured Sensors Enable Accurate Identification and Classification of Circulating Tumor Cells in Prostate Cancer Patient Blood Samples", Analytical Chemistry, 2013, vol. 85, No. 1, pp. 398-403.

Jackson, "Classical Electrodynamics", Third Edition, John Wiley & Sons, Inc., 1998, pp. 832. [Uploaded in 3 Parts].

Jang et al., "Optical Fiber SPR Biosensor with Sandwich Assay for the Detection of Prostate Specific Antigen", Optics Communications, Jul. 15, 2009, vol. 282, No. 14, pp. 2827-2830.

Jia et al., "Cerebrospinal Fluid tau, $A\beta 1$-42 and Inflammatory Cytokines in Patients with Alzheimer's Disease and Vascular Dementia", Neuroscience Letters, 2005, vol. 383, pp. 12-16.

Jiang et al., "Ultralow-Fouling, Functionalizable, and Hudrolyzable Zwitterionic Materials and Their Derivatives for Biological Applications", Advanced Materials, 2010, vol. 22, pp. 920-932.

Kajiura et al., "Biosensing by Optical Waveguide Spectroscopy Based on Localized Surface Plasmon Resonance of Gold Nanoparticles Used as a Probe or as a Label", Journal of Colloid and Interface Science, 2009, vol. 335, pp. 140-145.

Kaur et al., "Thermodynamic, Counterion, and Hydration Effects for the Incorporation of Locked Nucleic Acid Nucleotides into DNA Duplexes", Biochemistry, 2006, vol. 45, No. 23, pp. 7347-7355.

Khuseyinova et al., "Determination of C-Reactive Protein: Comparison of Three High-Sensitivity Immunoassays", Clinical Chemistry, 2003, vol. 49, No. 10, pp. 1691-1695.

Kim et al., "Preparation of Multivesicular Liposomes", Biochimica et Biophysica Acta (BBA)—Biomembranes, Mar. 9, 1983, vol. 728, No. 3, pp. 339-348.

(56)　　　　　References Cited

OTHER PUBLICATIONS

Kindt et al., "Chaperone Probes and Bead-Based Enhancement Improve the Direct Detection of mRNA Using Silicon Photonic Sensor Arrays", Analytical Chemistry, Sep. 18, 2012, vol. 84, No. 18, pp. 8067-8074.

Kindt et al., "Subpicogram Per Milliliter Detection of Interleukins Using Silicon Photonic Microring Resonators and an Enzymatic Signal Enhancement Strategy", Analytical Chemistry, 2013, vol. 85, pp. 10653-10657.

Kinney et al., "Monoclonal Antibody Assay for Detection of Double-Stranded RNA and Application for Detection of Group A and Non-Group A Rotaviruses", Journal of Clinical Microbiology, Jan. 1989, vol. 27, No. 1, pp. 6-12.

Koch et al., "Hurricane: A Simplified Optical Resonator for Optical-Power-Based Sensing With Nanoparticle Taggants", Sensors and Actuators B Chemical, 2010, vol. 147, pp. 573-580.

Kodadek et al., "Protein Microarrays: Prospects and Problems", Chemistry & Biology, 2001, vol. 8, pp. 105-115.

Kodadek et al., "Synthetic Molecules as Antibody Replacements", Accounts of Chemical Research, 2004, vol. 37, pp. 711-718.

Konry et al., "Microsphere-Based Rolling Circle Amplification Microarray for the Detection of DNA and Proteins in a Single Assay", Analytical Chemistry, 2009, vol. 81, No. 14, pp. 5777-5782.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", Tetrahedron, vol. 54, No. 14, Apr. 2, 1998, pp. 3607-3630.

Kostelny et al., "Formation of a Bispecific Antibody by the Use of Leucine Zippers", The Journal of Immunology, Mar. 1, 1992, vol. 148, No. 5, pp. 1547-1553.

Krasiński et al., "In Situ Selection of lead Compounds by Click Chemistry: Target-Guided Optimization of Acetylcholinesterase Inhibitors", Journal of the American Chemical Society, 2005, vol. 127, pp. 6686-6692.

Krioukov et al., "Sensor Based on an Integrated Optical Microcavity", Optics Letters, 2002, vol. 27, No. 7, pp. 512-514.

Krishnan et al., "Attomolar Detection of a Cancer Biomarker Protein in Serum by Surface Plasmon Resonance Using Superparamagnetic Particle Labels", Angewandte Chemie, Feb. 1, 2011, vol. 50, No. 5, pp. 1175-1178.

Krönke et al., "Sequential Expression of Genes Involved in Human T Lymphocyte Growth and Differentiation", Journal of Experimental Medicine, Jun. 1985, vol. 161, pp. 1593-1598.

Kumar et al., "The First Analogues of LNA (Locked Nucleic Acids): Phosphorothioate-LNA and 2'-thio-LNA", Bioorganic & Medicinal Chemistry Letters, vol. 8, No. 16, Aug. 18, 1998, pp. 2219-2222.

Ladd et al., "Zwitterionic Polymers Exhibiting High Resistance to Nonspecific Protein Adsorption from Human Serum and Plasma", Biomacromolecules, May 2008, vol. 9, No. 5, pp. 1357-1361.

Lafer et al., "The Effect of Anti-Z-DNA Antibodies on the B-DNA-Z-DNA Equilibrium", The Journal of Biological Chemistry, May 15, 1986, vol. 261, No. 14, pp. 6438-6443.

Lee et al., "Direct Measurement of the Forces Between Complementary Strands of DNA", Science, Nov. 4, 1994, vol. 266, No. 5186, pp. 771-773.

Lee et al., "MicroRNA Maturation: Stepwise Processing and Subcellular Localization", The EMBO Journal, 2002, vol. 21, No. 17, pp. 4663-4670.

Lee et al., "The C. Elegans Heterochronic Gene lin-4 Encodes Small RNAs with Antisense Complementarity to lin-14", Cell, Dec. 3, 1993, vol. 75, pp. 843-854.

Lee et al., "The Nuclear RNase III Drosha Initiates MicroRNA Processing", Letters to Nature, Sep. 25, 2003, vol. 425, pp. 415-419.

Li et al., "Detection of Protein biomarkers using RNA Aptamer Microarrays and Enzymatically Amplified SPR Imaging", Analytical Chemistry, Feb. 1, 2007, vol. 79, No. 3, pp. 1082-1088.

Li et al., "Real-Time Polymerase Chain Reaction MicroRNA Detection Based on Enzymatic Stem-Loop Probes Ligation", Analytical Chemistry, 2009, vol. 81, No. 13, pp. 5446-5451.

Li et al., "Sequence-Specific Label Free DNA Sensors Based on Silicon Nanowires", Nano Letters, Aug. 1, 2004, vol. 4, No. 2, pp. 245 to 247.

Lieberman et al., "Pharmaceutical Dosage Forms: Disperse Systems", Marcel Dekker Inc, Monticello, New York, U.S.A., 1988, Ch. 8, pp. 285-366.

Ligler F., "A Perspective on Optical Biosensors and Integrated Sensor Systems", Analytical Chemistry, Jan. 15, 2009, vol. 81, No. 2, pp. 519-526.

Lim et al., "Microarray Analysis Shows that some MicroRNAs Downregulate Large Numbers of Target mRNAs", Nature, Feb. 17, 2005, vol. 433, pp. 769-773.

Lin et al., "Myc-Regulated MicroRNAs Attenuate Embryonic Stem Cell Differentiation", The Embo Journal, 2009, vol. 28, pp. 3157-3170.

Little et al., "Microring Resonator Channel Dropping Filters," Journal of Lightwave Technology, Jun. 1997, vol. 15, No. 6, pp. 998-1005.

Lizardi et al., "Mutation Detection and Single-Molecule Counting Using Isothermal Rolling-Circle Amplification", Nature Genetics, 1998, vol. 19, pp. 225-232.

Llano et al., "Cerebrospinal Fluid Cytokine Dynamics Differ Between Alzheimer Disease Patients and Elderly Controls", Alzheimer Disease and Associated Disorders, Oct.-Dec. 2012, vol. 26, No. 4, pp. 322-328.

Lu et al., "MicroRNA Expression Profiles Classify Human Cancers", Nature, Jun. 9, 2005, vol. 435, pp. 834-838.

Luchansky et al., "Characterization of the Evanescent Field Profile and Bound Mass Sensitivity of a Label-Free Silicon Photonic Microring Resonator Biosensing Platform", Biosensors and Bioelectronics, Dec. 15, 2010, vol. 26, No. 4, pp. 1283-1291.

Luchansky et al., "Electronic Supplementary Information for: Sensitive On-Chip Detection of a Protein Biomarker in Human Serum and Plasma over an Extended Dynamic Range Using Silicon Photonic Microring Resonators and Sub-Micron Beads", Supplementary Material (ESI) for Lab on a Chip, The Royal Society of Chemistry, 2011, pp. 1-14.

Luchansky et al., "High-Q Optical Sensors for Chemical and Biological Analysis", Analytical Chemistry, Jan. 17, 2012, vol. 84, No. 2, pp. 793-821.

Luchansky et al., "Rapid, Multiparameter Profiling of Cellular Secretion using Silicon Photonic Microring Resonator Arrays", Journal of the American Chemical Society, Dec. 21, 2011, vol. 133, No. 50, pp. 20500-20506.

Luchansky et al., "Sensitive On-Chip Detection of a Protein Biomarker in Human Serum and Plasma over an Extended Dynamic Range Using Silicon Photonic Microring Resonators and Sub-Micron Beads", Lab Chip, Jun. 21, 2011, vol. 11, No. 12, pp. 2042-2044.

Luchansky et al., "Silicon Photonic Microring Resonators for Quantitative Cytokine Detection and T-Cell Secretion Analysis", Analytical Chemistry, Mar. 1, 2010, vol. 82, No. 5, pp. 1975-1981.

Luminex Corporation <http://www.luminexcorp.com/>, downloaded May 12, 2017 in 5 pages.

Luxton et al: "Use of External Magnetic Fields to Reduce Reaction Times in an Immunoassay Using Micrometer-Sized Paramagentic Particles as Labels (Magentoimmunoassay)", Analytical Chemistry, Mar. 15, 2004, vol. 76, pp. 1715-1719.

Mandal et al., "A Multiplexed Optofluidic Biomolecular Sensor for Low Mass Detection", Lab on a Chip, 2009, vol. 9, pp. 2924-2932.

Manetsch et al., "In Situ Click Chemistry: Enzyme Inhibitors Made to Their Own Specifications", Journal of the American Chemical Society, 2004, vol. 126, pp. 12809-12818.

Manger et al., "Differential Effect of Cyclosporin A on Activation Signaling in Human T Cell Lines", Journal of Clinical Investigation, May 1986, vol. 77, No. 5, pp. 1501-1506.

Martinez et al., "Increased Cerebrospinal Fluid Fas (Apo-1) Levels in Alzheimer's Disease. Relationship with IL-6 Concentrations", Brain Research, 2000, vol. 869, No. 1-2, pp. 216-219.

Marty et al., "Nonlinear Analyte Concentration Gradients for One-Step Kinetic Analysis Employing Optical Microring Resonators", Analytical Chemistry, Jul. 3, 2012, vol. 84, No. 13, pp. 5556-5564.

(56) References Cited

OTHER PUBLICATIONS

März et al., "Interleukin-6 (IL-6) and Soluble Forms of IL-6 Receptors are not Altered in Cerebrospinal Fluid of Alzheimer's Disease Patients", Neuroscience Letters, 1997, vol. 239, No. 1, pp. 29-32.

Mazur et al., "Concentration of IL-2, IL-6, IL-8, IL-10 and TNF-Alpha in Children with Acute Lymphoblastic Leukemia After Cessation of Chemotherapy", Hematological Oncology, 2004, vol. 22, No. 1, pp. 27-34.

McClellan et al., "Label-Free Virus Detection Using Arrays of Silicon Photonic Microring Resonators", Biosensors & Bioelectronics, Jan. 15, 2012, vol. 31, pp. 388-392.

Mckendry et al., "Multiple Label-Free Biodetection and Quantative DNA-Binding Assays on Nanomechanical Cantilever Array", Proceedings of the National Academy of Sciences of the United States of America (PNAS), Jul. 23, 2002, vol. 99, No. 15, pp. 9783 to 9788.

Meola et al., "MicroRNAs and Genetic Diseases", PathoGenetics, 2009, vol. 2, No. 7, pp. 1-14.

Moon et al., "A New Theranostic System Based on Gold Nanocages and Phase-Change Materials with Unique Features for Photoacoustic Imaging and Controlled Release", Journal of the American Chemical Society, Apr. 6, 2011, vol. 133, pp. 4762-4765.

Mudumba et al., "Photonic Ring Resonance is a Versatile Platform for Performing Multiplex Immunoassays in Real Time", Journal of Immunological Methods, 2017, vol. 448, pp. 34-43.

Munge et al., "Nanostructured Immunosensor for Attomolar Detection of Cancer Biomarker Interleukin-8 Using Massively Labeled Superparamagnetic Particles** ", Angewandte Chemie, Aug. 16, 2011, vol. 50, No. 34, pp. 7915-7918.

Murchison et al., "miRNAs on the Move: miRNA Biogenesis and the RNAi Machinery", Current Opinion in Cell Biology, Jun. 2004, vol. 16, No. 3, pp. 223-229.

Naffin et al., "Immobilized Peptides as High-Affinity Capture Agents for Self-Associating Proteins", Chemistry & Biology, Mar. 2003, vol. 10, pp. 251-259.

Nelson et al., "Microarray-Based, High-Throughput Gene Expression Profiling of MicroRNAs", Nature Methods, Nov. 2004, vol. 1, No. 2, pp. 155-161.

Nicoloso et al., "MicroRNAs—The Micro Steering Wheel of Tumour Metastases", Nature Reviews Cancer, 2009, pp. 9.

Nicoloso et al., "MicroRNAs: New Players in AML Pathogenesis", Cancer Treatment and Research, Jan. 1, 2010, vol. 145, pp. 169-181.

Nielsen et al., "Sequence-Selective Recognition of DNA by Strand Displacement with a Thymine-Substituted Polyamide", Science, Dec. 6, 1991, vol. 254, pp. 1497-1500.

Niemeyer et al., "Detecting Antigens by Quantitative Immuno-PCR", Nature Protocols, 2007, vol. 2, No. 8, pp. 1918-1930.

Niemeyer et al., "Semisynthetic DNA-Protein Conjugates for Biosensing and Nanofabrication", Angewandte Chemie, 2010, vol. 49, pp. 1200-1216.

O'Hara et al., "Cell-Surface and Cytokine Biomarkers in Autoimmune and Inflammatory Diseases", Drug Discovery Today, Apr. 2006, vol. 11, No. 7-8, pp. 342-347.

Ohtsuka et al., "Joining of Synthetic Ribotrinucleotides with Defined Sequences Catalyzed by T4 Rna Ligase", European Journal of Biochemistry, 1977, vol. 81, No. 2, pp. 285-291.

Olson et al., "Growth Factors and Cytokines/Chemokines as Surrogate Biomarkers in Cerebrospinal Fluid and Blood for Diagnosing Alzheimer's Disease and Mild Cognitive Impairment", Experimental Gerontology, 2010, vol. 45, pp. 41-46.

Ørom et al., "MicroRNA-10a Binds the 5'UTR of Ribosomal Protein mRNAs and Enhances Their Translation", Molecular Cell, May 23, 2008, vol. 30, 460-471.

Orsilles et al., "IL-2 and IL-10 Serum Levels in HIV-1-Infected Patients with or Without Active Antiretroviral Therapy", APMIS, Jan. 2006, vol. 114, No. 1, pp. 55-60.

Ørum et al., "Locked Nucleic Acids: A Promising Molecular Family for Gene-Function Analysis and Antisense Drug Development", Current Opinion in Molecular Therapeutics, Jun. 2001, vol. 3, No. 3, pp. 239-243.

Palandra et al., "Highly Specific and Sendsitive Measurements of Human and Monkey Interleukin 21 Using Sequential Protein and Tryptic Peptide Immunoaffinity LC-MS/MS", Analytical Chemistry, 2013, vol. 85, pp. 5522-5529.

Palik, Edward D., "Handbook of Optical Constants of Solids III", Academic Press, 1998, Ch. 1, pp. 1-12.

Parker et al., "Monoclonal Antibodies Against the Human Epidermal Growth Factor Receptor from A431 Cells. Isolation, Characterization, and use in the Purification of Active Epidermal Growth Factor Receptor", The Journal of Biological Chemistry, 1984, vol. 259, pp. 9906-9912.

Pérez-Luna, "Molecular Recognition between Genetically Engineered Streptavidin and Surface-Bound Biotin", Journal of the American Chemical Society, 1999, vol. 121, pp. 6469-6478.

Phelan et al., "Generation of Bioreagents for Protein Chips", Proteomics, 2003, vol. 3, pp. 2123-2134.

Pierres et al., "Dissecting Steptavidin-Biotin Interaction with a Laminar Flow Chamber", Biophysical Journal, Jun. 2002, vol. 82, pp. 3214-3223.

Poethig, R. Scott, "Small RNAs and Developmental Timing in Plants", Current Opinion in Genetics & Development, Aug. 2009, vol. 19, No. 4, pp. 374-378.

Poy et al., "A Pancreatic Islet-Specific MicroRNA Regulates Insulin Secretion", Nature, 2004, vol. 432, No. 7014, pp. 226-230.

Puchner et al., "Force and Function: Probing Proteins with AFM-Based Force Spectroscopy", Current Opinion in Structural Biology, 2009, vol. 19, pp. 605-614.

Qavi et al., "Anti-DNA:RNA Antibodies and Silicon Photonic Microring Resonator Arrays Enable the Ultrasensitive, Multiplexed Detection of microRNAs", Analitical Chemistry, Aug. 1, 2011, vol. 83, No. 15, pp. 5949-5956.

Qavi et al., "Isothermal Discrimination of Single Nucleotide Polymorphisms via Real-Time Kinetic Desorption and Label-Free Detection of DNA Using Silicon Photonic Microring Resonator Arrays", Analytical Chemistry, 2011, vol. 83, pp. 6827-6833.

Qavi et al., "Label-Free Technologies for Quantitative Multiparameter Biological Analysis", Analytical BioAnalytical Chemistry, May 2009, vol. 394, No. 1, pp. 121-135.

Qavi et al., "Multiplexed Detection and Label-Free Quantitation of MicroRNAs Using Arrays of Silicon Photonic Microring Resonators", Angewandte Chemie International Edition, Jun. 21, 2010, vol. 49, No. 27, pp. 4608-4611.

Ramachandran et al., "A Universal Biosensing Platform Based on Optical Micro-Ring Resonators", Biosensors and Bioelectronics, 2008, vol. 23, pp. 939-944.

Reddy et al., "Transformation of Low-Affinity Lead Compounds into High-Affinity Protein Capture Agents", Chemistry & Biology, Aug. 2004, vol. 11, pp. 1127-1137.

Riley et al., "Stability of DNA/anti-DNA complexes: II. Salt Lability and Avidity", The Journal of Immunology, Jan. 1980, vol. 124, No. 1, pp. 1-7.

Rissin et al., "Single-Molecule Enzyme-Linked Immunosorbent Assay Detects Serum Proteins at Subfemtomolar Concentrations", Nature Biotechnology, Jun. 2010, vol. 28, No. 6, pp. 595-599.

Roberts, Peter, "MicroRNA Expression Profiling on Arrays Enhanced with Locked Nucleic Acids", Nature Methods, Exiqon, Apr. 2006, pp. iii-iv.

Roblin et al., "Combination of C-reactive Protein, Infliximab Trough Levels, and Stable but Not Transient Antibodies to Infliximab Are Associated With Loss of Response to Infliximab in Inflammatory Bowel Disease", Journal of Crohn's and Colitis, Apr. 2015, pp. 525-531.

Rockwell et al., "A COX-2 Metabolite of the Endogenous Cannabinoid, 2-Arachidonyl Glycerol, Mediates Suppression of IL-2 Secretion in Activated Jurkat T Cells", Biochemical Pharmacology, Aug. 1, 2008, vol. 76, No. 3, pp. 353-361.

Romaniuk et al., "The Effect of Acceptor Oligoribonucleotide Sequence on the $T_4$ RNA Ligase Reaction", European Journal of Biochemistry, 1982, vol. 125, pp. 639-643.

SABiosciences, "Single Analyte ELISA Kits", Product List, 2010, <http://www.sabiosciences.com/singleelisa.php>, as printed Jun. 1, 2015 in 2 pages.

(56) References Cited

OTHER PUBLICATIONS

Sano et al., "Immuno-PCR: Very Sensitive Antigen Detection by Means of Specific Antibody-DNA Conjugates", Science, Oct. 2, 1992, vol. 258, No. 5079, pp. 120-122.

Scheck et al., "Regioselective Labeling of Antibodies through N-Terminal Transamination", ACS Chemical Biology, 2007, vol. 2, pp. 247-251.

Scheler et al., "Label-Free, Multiplexed Detection of Bacterial tmRNA Using Silicon Photonic Microring Resonators", Biosensors & Bioelectronics, 2012, vol. 36, No. 1, pp. 56-61.

Schmidt, Jacob, "Stochastic Sensors", Journal of Materials Chemistry, 2005, vol. 15, pp. 831-840.

Schratt et al., "A Brain-Specific MicroRNA Regulates Dendritic Spine Development", Nature, Jan. 19, 2006, vol. 439, No. 7074, pp. 283-289.

Schüler et al., "A Disposable and Cost Efficient Microfluidic Device for the Rapid Chip-Based Electrical Detection of DNA", Biosensors and Bioelectronics, 2009, vol. 25, pp. 15-21.

Schwelb, Dr. Otto, "The Vernier Principle in Photonics", Concordia University, published May 6, 2011, pp. 4.

Sempere et al., "Expression Profiling of Mammalian MicroRNAs Uncovers a Subset of Brain-Expressed MicroRNAs with Possible Roles in Murine and Human Neuronal Differentiation", Genome Biology, Article R13, 2004, vol. 5, No. 3, pp. 11.

Severin et al., "A High Throughput Molecular Force Assay for Protein-DNA Interactions", Lab on a Chip, 2011, vol. 11, pp. 856-862.

Sheehan et al., "Detection Limits for Nanoscale Biosensors" Nano Letters, 2005, vol. 5, No. 4, pp. 803-807.

Shi, Yang, "Mammalian RNAi for the Masses", Trends in Genetics, Jan. 2003, vol. 19, No. 1, pp. 9-12.

Shia et al., "Single Domain Antibodies for the Detection of Ricin Using Silicon Photonic Microring Resonator Arrays", Analytical Chemistry, Jan. 2013, vol. 85, No. 2, pp. 805-810.

Shopova, "On-Column Micro-Gas-Chromatography Detection with Capillary Based Optical Ring Resonators", Analytical Chemistry, 2008, vol. 80, pp. 2232-2238.

Siegman, Anthony E., "Lasers", University Science Books, 1986, pp. 1283. [Uploaded in 2 parts].

SIGMA®, "Product Information", P 1585 Datasheet, Sigma-Aldrich, Inc., 2002, <https://www.sigmaaldrich.com/content/dam/sigma-aldrich/docs/Sigma/Datasheet/4/p1585dat.pdf>, p. 1.

Singh et al., "Synthesis of 2'-Amino-LNA: A Novel Conformationally Restricted High-Affinity Oligonucleotide Analogue with a Handle", The Journal of Organic Chemistry, 1998, vol. 63, No. 26, p. 10035-10039.

Šípová et al., "Surface Plasmon Resonance Biosensor for Rapid Label-Free Detection of Microrna at Subfemtomole Level", Analytical Chemistry, Dec. 15, 2010, vol. 82, No. 24, pp. 10110-10115.

Sklar et al., "Flow Cytometric Analysis of Ligand-Receptor Interactions and Molecular Assemblies", Annual Review of Biophysics and Biomolecular Structure, Feb. 2002, vol. 31, No. 1, pp. 97-119.

Sloan et al., "Interfacing Lipid Bilayer Nanodiscs and Silicon Photonic Sensor Arrays for Multiplexed Protein-Lipid and Protein-Membrane Protein Interaction Screening", Analytical Chemistry, Mar. 5, 2013, vol. 85, No. 5, pp. 2970-2976.

Smith, K.A., "Interleukin-2: Inception, Impact, and Implications", Science, May 27, 1988, vol. 240, No. 4856, pp. 1169-1176.

Söderberg et al., "Proximity Ligation: A Specific and Versatile Tool for the Proteomic Era", Genetic Engineering, 2007, vol. 28, pp. 85-93.

Soelberg et al., "Surface Plasmon Resonance (SPR) Detection Using Antibody-Linked Magnetic Nanoparticles for Analyte Capture, Purification, Concentration and Signal Amplification", Analytical Chemistry, Mar. 15, 2009, vol. 81, No. 6, pp. 2357-2363.

Sokolova et al., "Monocyte Chemoattractant Protein-1 Plays a Dominant Role in the Chronic Inflammation Observed in Alzheimer's Disease", Brain Pathology, 2009, vol. 19, No. 3, pp. 392-398.

Soleymani et al., "Hierarchical Nanotextured Microelectrodes Overcome the Molecular Transport Barrier To Achieve Rapid, Direct Bacterial Detection", ACS Nano, 2011, vol. 5, No. 4, pp. 3360-3366.

Solulink, <https://web.archive.org/web/20100719122056/http://www.solulink.com/>, as archived Jul. 19, 2010, pp. 2.

Song et al., "Detection of Oligonucleotide Hybridization at Femtomolar Level and Sequence-Specific Gene Analysis of the *Arabidopsis thaliana* Leaf Extract with an Ultrasensitive Surface Plasmon Resonance Spectrometer", Nucleic Acids Research, 2002, vol. 30, No. 14 e72, pp. 1-11.

Squires et al., "Making it Stick: Convection, Reaction and Diffusion in Surface-Based Biosensors", Nature Biotechnology, Apr. 2008, vol. 26, No. 4, pp. 417-426.

Steenholdt et al., "Clinical Implications of Measuring Drug and Anti-Drug Antibodies by Different Assays when Optimizing Infliximab Treatment Failure in Crohn's Disease: Post Hoc Analysis of a Randomized Controlled Trial", American Journal of Gastroenterology, Jul. 2014, vol. 109, No. 7, pp. 1055-1064.

Steensberg et al., "Cerebrospinal Fluid IL-6, HSP72, and TNF-$\alpha$ in Exercising Humans", Brain Behavior and Immunity, 2006, vol. 20, pp. 585-589.

Stelmasiak et al., "Interleukin-6 Concentration in Serum and Cerebrospinal Fluid in Multiple Sclerosis Patients", Medical Science Monitor, 2000, vol. 6, No. 6, pp. 1104-1108.

Stollar et al., "Immunochemical Approaches to Gene Probe Assays", Analytical Biochemistry, 1987, vol. 161, No. 2, pp. 387-394.

Stollar, B. David, "Molecular Analysis of Anti-DNA Antibodies", The FASEB Journal, Mar. 1994, vol. 8, No. 3, pp. 337-342.

Streit et al., "Northern Blot Analysis for detection and Quantification of RNA in Pancreatic Cancer Cells and Tissues", Nature Protocols, 2009, vol. 40, No. 1, pp. 37-43.

Stroock et al., "Chaotic Mixer for Microchannels", Science, Jan. 25, 2002, vol. 295, pp. 647-651.

Stuart et al., "Biological Applications of Localised Surface Plasmonic Phenomenae", IEE Proceedings—Nanobiotechnology, Feb. 2005, vol. 152, No. 1, pp. 13-32.

Su et al., "Site-Specific Labelling of Proteins with a Rigid Lanthanide-Binding Tag", ChemBioChem, 2006, vol. 7, pp. 1599-1604.

Sun et al., "Effect of Fluorescently Labeling Protein Probes on Kinetics of Protein-Ligand Reactions", Langmuir, Dec. 2, 2008, vol. 24, No. 23, pp. 13399-13405.

Sundrud et al., "Inhibition of Primary Human T Cell Proliferation by *Helicobacter pylori* Vacuolating Toxin (VacA) is Independent of VacA Effects on IL-2 Secretion", Proceedings of the National Academy of Sciences of the United States of America (PNAS), May 18, 2004, vol. 101, No. 20, 7727-7732.

Suter et al., "Label-Free Quantitative DNA Detection Using the Liquid Core Optical Ring Resonator", Biosensors and Bioelectronics, Feb. 28, 2008, vol. 23, No. 7, pp. 1003-1009.

Székvölgyi et al., "Ribonucleoprotein-Masked Nicks at 50-kbp Intervals in the Eukaryotic Genomic DNA", Proceedings of the National Academy of Sciences of the United States of America (PNAS), Sep. 18, 2007, vol. 104, No. 38, pp. 14964-14969.

Szoka, Jr., Francis, "Comparative Properties and Methods of Preparation of Lipid Vesicles (Liposomes)", Annual Review of Biophysics and Bioengineering, 1980, vol. 9, pp. 467-508.

Tarkowski et al., "Early Intrathecal Production of Interleukin-6 Predicts the Size of Brain Lesion in Stroke", Stroke, 1995, vol. 26: 1393-1398.

Tarkowski et al., "Intracerebral Production of Tumor Necrosis Factor-$\alpha$, a Local Neuroprotective Agent, in Alzheimer Disease and Vascular Dementia," Journal of Clinical Immunology, Jul. 1999, vol. 19, No. 4, pp. 223-230.

Thaxton et al., "Optically and Chemically Encoded Nanoparticle Materials for DNA and Protein Detection", MRS Bulletin, May 2005, vol. 30, pp. 376-380.

Tsai et al., "Cerebrospinal Fluid Interleukin-6, Prostaglandin E2 and Autoantibodies in Patients with Neuropsychiatric Systemic Lupus Erythematosus and Central Nervous System Infections", Scandinavian Journal of Rheumatology, 1994, vol. 23, No. 2, pp. 57-63.

US 12,566,140 B2

Page 9

(56) References Cited

OTHER PUBLICATIONS

Tsai et al., "MicroRNAs in Common Diseases and Potential Therapeutic Applications", Clinical and Experimental Pharmacology and Physiology, 2010, vol. 37, No. 1, pp. 102-107.
Tuerk et al., "Systematic Evolution of Ligands by Exponential Enrichment: RNA Ligands to Bacteriophage T4 DNA Polymerase", Science, Aug. 3, 1990, vol. 249, No. 4968, pp. 505-510.
Turner et al., "Chemical Cytometry: The Chemical Analysis of Single Cells", Analytical BioAnalytical Chemistry, 2008, vol. 390, pp. 223-226.
Tutt et al., "Trispecific F(ab')3 Derivatives that use Cooperative Signaling Via the TCR-CD3 Complex and CD2 to Activate and Redirect Resisting Cytotoxic T Cells", The Journal of Immunology, Jul. 1, 1991, vol. 147, No. 1, pp. 60-69.
Vahala, Kerry, "Optical Microcavities", Nature, Aug. 14, 2003, vol. 424, pp. 839-846.
Vandermeeren et al., "Detection of τ Proteins in Normal and Alzheimer's Disease Cerebrospinal Fluid with a Sensitive Sandwich Enzyme-Linked Immunosorbent Assay", Journal of Neurochemistry, 1993, vol. 61, No. 5, pp. 1828-1834.
Varkonyi-Gasic et al., "Protocol: a Highly Sensitive RT-PCR Method for Detection and Quantification of MicroRNAs", Plant Methods, 2007, vol. 3, pp. 12.
Veeramachaneni et al., "Analysis of Forces Acting on Superparamagnetic Beads in Fluid Medium in Gradient Magnetic Fields", Excerpt from the Proceedings of the COMSOL Conference 2009 Boston, pp. 5.
Veitch, Nigel C., "Horseradish Peroxidase: A Modern View of a Classic Enzyme", Phytochemistry, 2004, vol. 65, No. 3, pp. 249-259.
Vollmer et al., "Multiplexed DNA Qualification by Spectoscopic Shift of Two Microsphere Cavities", Biophysical Journal, Sep. 2003, vol. 85, pp. 1974 to 1979 [See pp. 1974 to 1977].
Vollmer et al., "Protein Detection by Optical Shift of a Resonant Microcavity", Applied Physics Letters, May 27, 2002, vol. 80, No. 21, pp. 4057-4059.
Vollmer et al., "Single Virus Detection from the Reactive Shift of a Whispering-Gallery Mode", Proceedings of the National Academy of Sciences of the United States of America (PNAS), Dec. 30, 2008, vol. 105, No. 52, pp. 20701-20704.
Vollmer et al., "Whispering-Gallery-Mode Biosensing: Label-Free Detection Down to Single Molecules", Nature Methods, Jul. 2008, vol. 5, No. 7, pp. 591-596.
Wang et al., "Cell Cycle Regulation by MicroRNAs in Embryonic Stem Cells", Cancer Research, May 15, 2009, vol. 69, No. 10, pp. 4093-4096.
Wang et al., "Cyclohexene Nucleic Acids (CeNA): Serum Stable Oligonucleotides that Activate RNase H and Increase Duplex Stability with Complementary RNA", Journal of the American Chemical Society, 2000, vol. 122, No. 36, pp. 8595-8602.
Wang et al., "Magnetic Nanoparticle-Enhanced Biosensor Based on Grating-Coupled Surface Plasmon Resonance", Analytical Chemistry, 2011, vol. 83, pp. 6202-6207.
Washburn et al., "DNA-Encoding of Antibodies Improves Performance and Allows Parallel Evaluation of the Binding Characteristics of Multiple Protein Capture Agents in a Surface-Bound Immunoassay Format", Analytical Chemistry, May 1, 2011, vol. 83, No. 9, pp. 3572-3580.
Washburn et al., "Label-Free Quantitation of a Cancer Biomarker in Complex Media using Silicon Photonic Microring Resonators", Analytical Chemistry, Nov. 15, 2009, vol. 81, No. 22, pp. 9499-9506.
Washburn et al., "Photonics-on-a-Chip: Recent Advances in Integrated Waveguides as Enabling Detection Elements for Real-World, Lab-on-a-Chip Biosensing Applications", Analyst, Jan. 21, 2011, vol. 136, No. 2, pp. 227-236.
Washburn et al., "Quantitative, Label-Free Detection of Five Protein Biomarkers Using Multiplexed Arrays of Silicon Photonic Microring Resonators", Analytical Chemistry, 2010, vol. 82, pp. 69-72.

Watercampws, <https://web.archive.org/web/20100614031023/http://www.watercampws.uiuc.edu/waterclear/labs/>, as archived Jun. 14, 2010, pp. 2.
Wayment et al., "Controlling Binding Site Densities on Glass Surfaces", Analytical Chemistry, 2006, vol. 78, pp. 7841-7849.
Weiss et al., "The Role of T3 Surface Molecules in the Activation of Human T Cells: A Two-Stimulus Requirement for IL 2 Production Reflects Events Occurring at a Pre-Translational Level", The Journal of Immunology, Jul. 1984, vol. 133, No. 1, pp. 123-128.
White et al., "Label-Free Detection with the Liquid Core Optical Ring Resonator Sensing Platform", Methods in Molecular Biology, 2009, vol. 503, pp. 139-165.
Williams et al., "A Practical Guide to the Staggered Herringbone Mixer", Lab on a Chip, 2008, vol. 8, No. 7, pp. 1121-1129.
Wolfbeis et al., "Fiber-Optic Chemical Sensors and Biosensors", Analytical Chemistry, 2002, vol. 74, pp. 2663-2678.
Wolter et al., "Preparation and Characterization of Functional Poly(ethylene glycol) Surfaces for the Use of Antibody Microarrays", Analytical Chemistry, 2007, vol. 79, pp. 4529-4537.
Wu et al., "Multiple MicroRNAs Modulate p21Cip1/Waf1 Expression by Directly Targeting its 3' Untranslated Region", Oncogene, 2010, vol. 29, pp. 2302-2308.
Xu et al., "Folded Cavity SOI Microring Sensors for High Sensitivity and Real Time Measurement of Biomolecular Binding", Optics Express, Sep. 15, 2008, vol. 16, No. 19, pp. 15137-15148.
Yang et al., "Detection of Picomolar Levels of Interleukin-8 in Human Saliva by SPR", Lab on a Chip, Oct. 2005, vol. 5, No. 10, pp. 1017-1023.
Yang et al., "Direct, Electronic MicroRNA Detection for the Rapid Determination of Differential Expression Profiles", Angewandte Chemie International Edition, 2009, vol. 48, pp. 5.
Young et al., "Cytokine Multiplex Analysis", Inflammation and Cancer, Methods in Molecular Biology, 2009, Ch. 4, vol. 511, pp. 85-105.
Zhu et al., "A Microdevice for Multiplexed Detection of T-Cell-Secreted Cytokines", Lab on a Chip, Dec. 2008, vol. 8, pp. 2197-2205.
Zhu et al., "Opto-Fluidic Micro-Ring Resonator for Sensitive Label-Free Viral Detection", Analyst, 2008, vol. 133, pp. 356-360.
Zhu et al., "Rapid and Label-Free Detection of Breast Cancer Biomarker CA15-3 in Clinical Human Serum Samples with Optofluidic Ring Resonator Sensors", Analytical Chemistry, 2009, vol. 81, No. 24, pp. 9858-9865.
International Search Report received in PCT Application No. PCT/US2009/062268, dated Jun. 16, 2010.
International Preliminary Report on Patentability and Written Opinion received in PCT Application No. PCT/US2009/062268, dated May 12, 2011.
International Search Report received in PCT Application No. PCT/US2011/059454, dated Jun. 1, 2012.
International Preliminary Report on Patentability and Written Opinion received in PCT Application No. PCT/US2011/059454, dated May 16, 2013.
International Search Report and Written Opinion received in PCT Application No. PCT/US2008/085988, dated May 26, 2009.
International Preliminary Report on Patentability and Written Opinion received in PCT Application No. PCT/US2008/085988, dated Jun. 8, 2010.
International Search Report and Written Opinion received in PCT Application No. PCT/US2013/030274, dated May 24, 2013.
International Preliminary Report on Patentability and Written Opinion received in PCT Application No. PCT/US2013/030274, dated Sep. 25, 2014.
International Search Report and Written Opinion received in PCT Application No. PCT/US2014/026852, dated Jun. 16, 2014.
International Preliminary Report on Patentability and Written Opinion received in PCT Application No. PCT/US2014/026852, dated Sep. 24, 2015.
International Search Report and Written Opinion received in PCT Application No. PCT/US2019/029740, dated Jul. 10, 2019.

(56)  References Cited

OTHER PUBLICATIONS

International Search Report and Written Opinion received in PCT Application No. PCT/US2021/025456, dated Jul. 22, 2021.

* cited by examiner

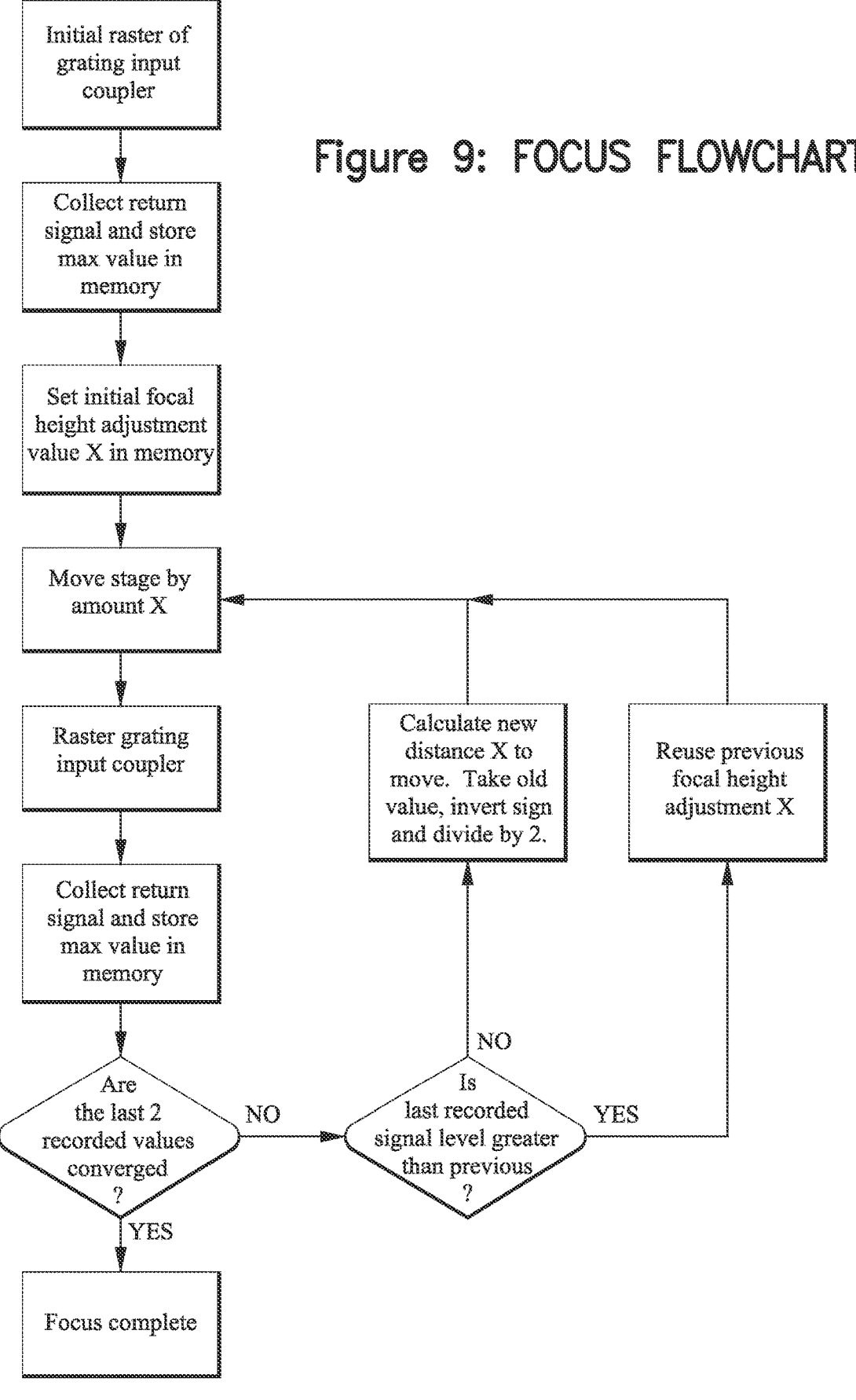
Figure 9: FOCUS FLOWCHART

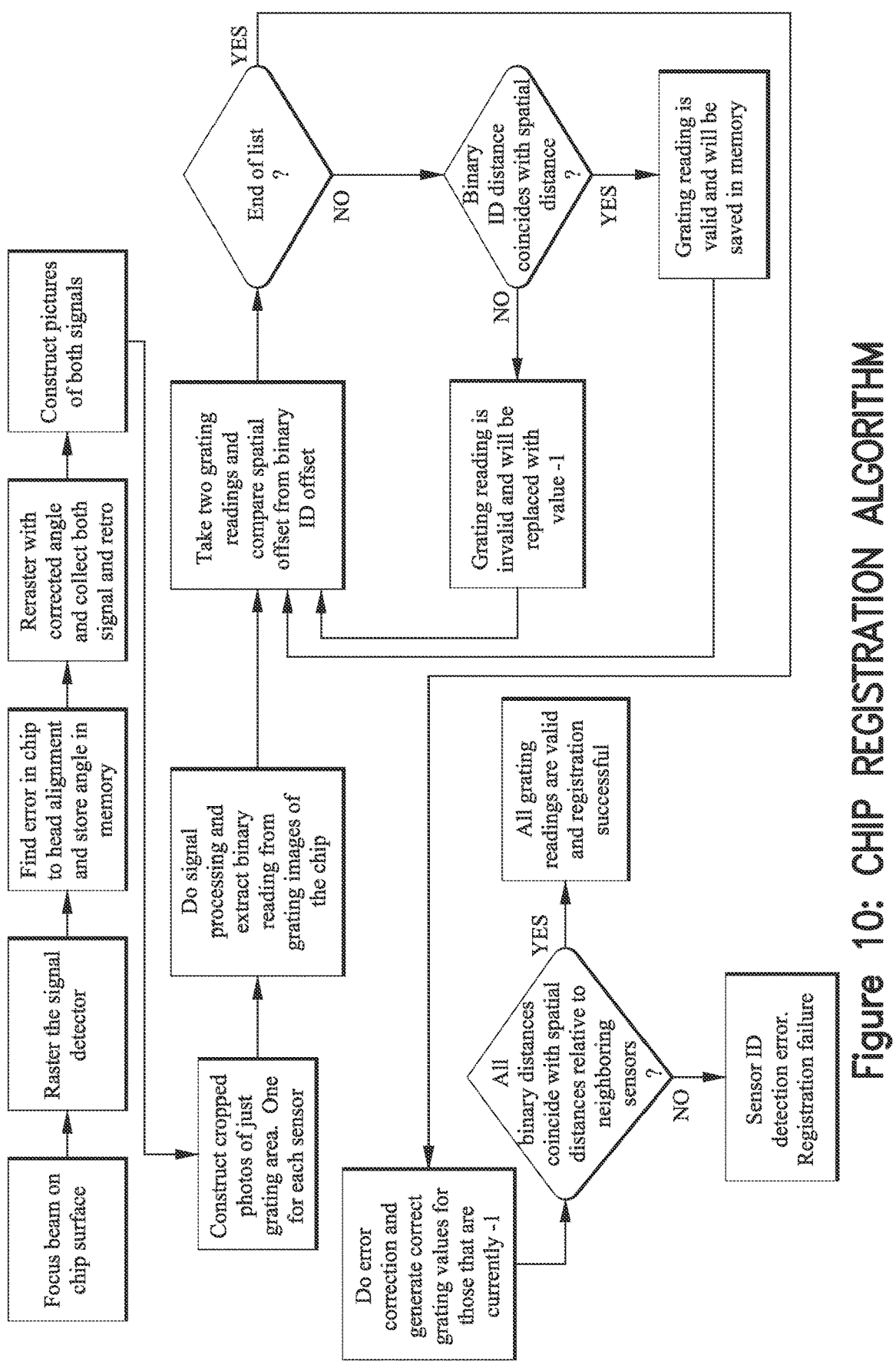
Figure 10: CHIP REGISTRATION ALGORITHM

Figure 11: SENSOR IMAGE

Figure 12: Exemplary image of on-chip gratings

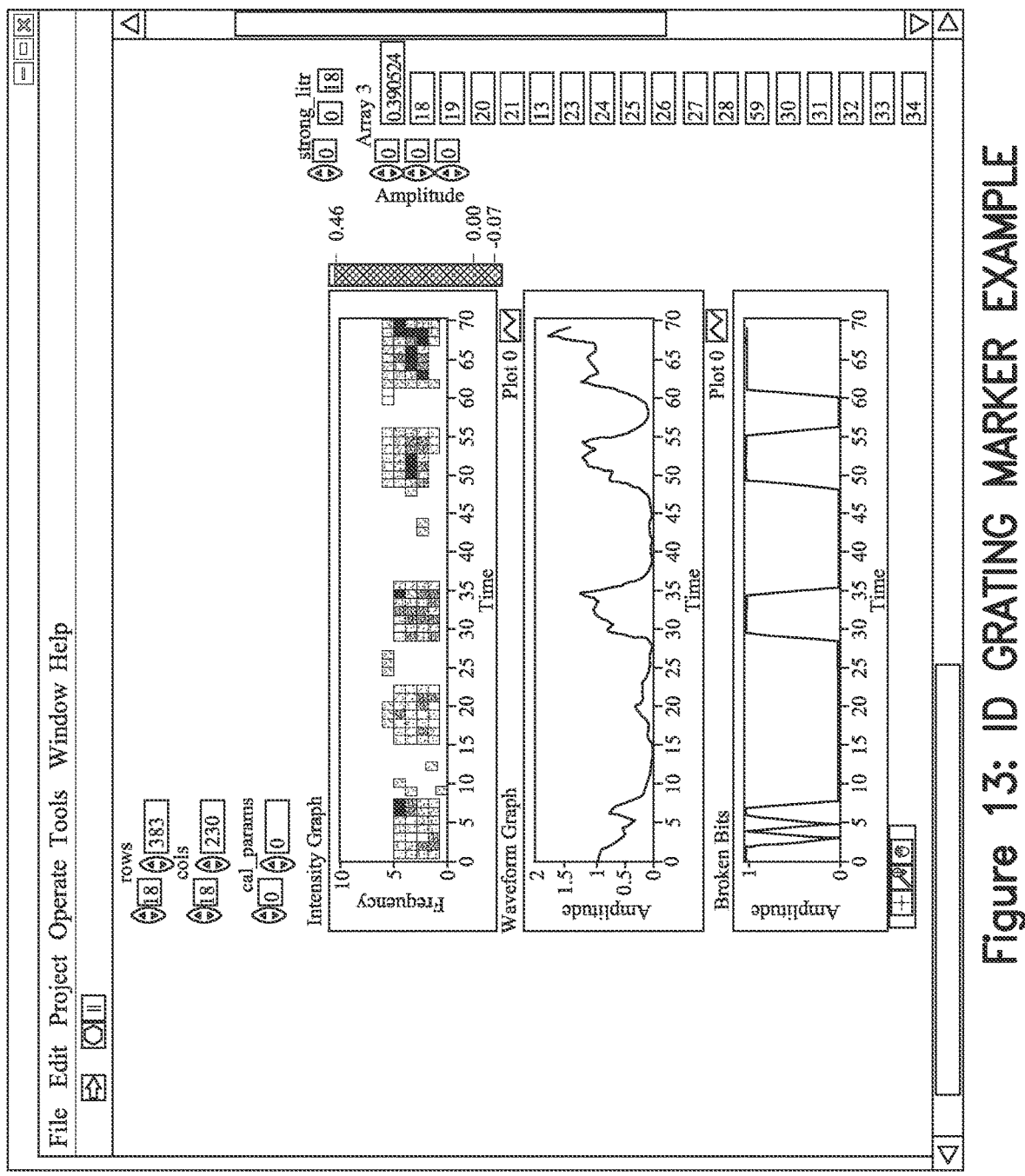
Figure 13: ID GRATING MARKER EXAMPLE

Figure 14: Representation of Tracking Algorithm 6 intentionally offset points centered around the Last best test point Last best test point

BIOSENSORS BASED ON OPTICAL PROBING AND SENSING

INCORPORATION BY REFERENCE TO ANY PRIORITY APPLICATIONS

This application is a continuation of U.S. patent application Ser. No. 15/844,306, filed Dec. 15, 2017, and entitled "BIOSENSORS BASED ON OPTICAL PROBING AND SENSING," which is a continuation of U.S. patent application Ser. No. 13/126,164, filed Jul. 18, 2011, and entitled "BIOSENSORS BASED ON OPTICAL PROBING AND SENSING," which is a national phase of PCT/US2009/062268, filed Oct. 27, 2009, and entitled "BIOSENSORS BASED ON OPTICAL PROBING AND SENSING," which claims priority to U.S. Provisional Patent Application No. 61/108,862, filed Oct. 27, 2008, and entitled "BIOSENSORS BASED ON OPTICAL PROBING AND SENSING." All of the foregoing applications, and any other application for which a foreign or domestic priority claim is identified in the Application Data Sheet as filed with the present application, are hereby incorporated by reference under 37 CFR 1.57.

BACKGROUND

Field

This document relates to optical sensing of substances, including biological and chemical substances.

Description of the Related Art

Optical properties of certain optical elements, such as optical resonators and waveguides, may be used for detecting substances attached to such optical elements. Probe light is directed to the areas where substances to be measured are present in or near the optical elements and optical measurements are performed at such optical elements to detect the substances.

SUMMARY

This document describes apparatus, sensor chips and techniques for optical sensing of substances by using optical sensors on sensor chips.

In one aspect, a sensing device based on optical probing and sensing includes a tunable laser that produces a laser beam of the probe light and operates to tune a wavelength of the probe light over different wavelengths and a chip platform that holds one or more sensor chips under measurement. Each sensor chip includes a substrate, one or more optical sensors formed on the substrate, an input optical coupler formed on the substrate to receive and direct the probe light to a respective optical sensor, and an output optical coupler formed on the substrate to couple light from the respective optical sensor out of the substrate as returned probe light. An optical system is provided to project and scan the probe light over the chip platform to optically interrogate optical sensors on a sensor chip. The optical system includes an objective lens oriented relative to the chip platform at an angle to render specular reflection of the probe light from the sensor chip outside an optical aperture of the objective lens and to receive the returned probe light from the sensor chip at a direction different from the specular reflection of the probe light from the sensor chip. This device includes an optical detector in communication with the optical system to receive a portion of the returned probe light and to detect responses of each optical sensor on a sensor chip over different wavelengths of the tunable laser.

In another aspect, a sensing chip for optical probing and sensing is provided to include a substrate; optical sensors formed at different locations on the substrate, and optical waveguides formed on the substrate and optically coupled to the optical sensors, respectively. Each optical waveguide couples light into a respective optical sensor and to couple light out of the respective optical sensor. This chip includes input optical couplers formed on the substrate and coupled to the optical waveguides, respectively and each input optical coupler receives probe light incident onto the substrate from the air and directs the received probe light into a respective optical waveguide coupled to a respective optical sensor. Output optical couplers are formed on the substrate and coupled to the optical waveguides, respectively. Each output optical coupler couples light guided by a respective optical waveguide from a respective optical sensor into a returned probe light directed into the air. This chip includes optical identification markers formed on the substrate at locations adjacent to the optical couplers, respectively, so that each optical identification marker is uniquely associated with a respective optical sensor. Each optical identification marker is structured to have a unique code for identifying the respective optical sensor and optically interacting with the probe light to produce a returned identification light carrying the code.

In another aspect, a sensing device based on optical probing and sensing is provided to include a tunable laser that produces a laser beam of the probe light and operates to tune a wavelength of the probe light over different wavelengths and a chip platform that holds one or more sensor chips under measurement. Each sensor chip comprises a substrate, optical sensors formed at different locations on the substrate that receive probe light and produce returned probe light, and optical identification markers formed on the substrate at locations that uniquely associate each optical identification marker with a respective optical sensor and is structured to have a unique code for identifying the respective optical sensor and optically interacting with the probe light to produce a returned identification light carrying the code. An optical system in this device projects and scans the probe light over the chip platform to optically interrogate optical sensors on a sensor chip, and receives returned probe light from the sensor chip. The optical system includes a beam splitter that splits the returned probe light into a first portion and a second portion. This device includes a first optical detector in communication with the optical system to receive the first portion of the returned probe light and to detect responses of each optical sensor on a sensor chip over different wavelengths of the tunable laser; and a second optical detector in communication with the optical system to receive the second portion of the returned probe light and to detect at least the identification codes of different optical identification markers.

In another aspect, a method for optical sensing is provided to include directing probe light from a tunable laser via free space onto a sensor chip. This sensor chip includes a substrate, optical sensors formed at different locations on the substrate, an input optical coupler formed on the substrate to receive and direct the probe light to a respective optical sensor, and an output optical coupler formed on the substrate to couple light from the respective optical sensor out of the substrate as returned probe light at a direction different from specular reflection of the probe light produced by the sensor chip. In this method, the returned probe light from the sensor chip is collected while rejecting the specular reflection of the probe light from the sensor chip, the probe light is spatially scanned to optically address different optical sensors on the sensor chip, one optical sensor at a time to obtain responses from each optical sensor while tuning the tunable laser over different wavelengths of the tunable laser, and responses from each optical sensor over the different wavelengths of the tunable laser are processed to measure one or more substances attached to the optical sensor.

In another aspect, a sensing device based on optical probing and sensing includes a chip comprising a substrate, microstructures formed on the substrate, and input optical couplers respectively formed on the substrate to receive probe light and to direct the received probe light to the microstructures, respectively; a tunable laser located outside the chip to produce a beam of the probe light and operable to tune a wavelength of the probe light; and an optical coupling module located in an optical path of the probe light between the tunable laser and the chip to direct the probe light from the tunable laser onto the chip.

In another aspect, a sensing device based on optical probing and sensing is provided to include a tunable laser that produces a laser beam of the probe light and operates to tune a wavelength of the probe light over different wavelengths and a chip platform that holds one or more sensor chips under measurement. Each sensor chip includes a substrate, optical sensors formed at different locations on the substrate that receive probe light and produce returned probe light. An optical system is included in the device to project the probe light over the chip platform to optically interrogate optical sensors on a sensor chip. The optical system includes one or more scanning mirrors that scan the probe light over the sensor chip to direct the probe light to the optical sensors, one optical sensor at a time and different optical sensors at different times during scanning, and an objection lens that receives the scanning probe light from the one or more scanning mirrors and directs the scanning probe light onto the sensor chip. The device includes an optical detector in communication with the optical system to receive a portion of the returned probe light and to detect responses of each optical sensor on a sensor chip over different wavelengths of the tunable laser.

In another aspect, an optical wavelength scanning system is provided for determining the resonant frequency and/or lineshape of an optical cavity comprising a tunable wavelength source which is sent partially to a wavelength referencing system comprising an etalon or gas cell and partially to the resonant cavity, the optical output of each path being directed to one of a pair of time synchronized photoreceivers.

In another aspect, an optical system is provided for interrogating a biosensor chip where the input signal and the return signal transmit through a portion of the total optical path in opposite directions and where the input signal and the return signal are both at an angle to the normal of the sensor chip, and where the specular reflection signal off the sensor chip falls outside of the numerical aperture of the optical system.

In another aspect, an optical system is provided for interrogating a biosensor chip where the input signal and the return signal transmit through a portion of the total optical path in opposite directions and where a spatial filter, such as a pinhole, is used to block all light except the return signal from falling on the photoreceiver.

In another aspect, an optical system is provided for scanning a biosensor chip comprising a steering mirror located at the front focal length of an objective lens such that the chief ray of the output beam will be maintained constant as the location of the output beam is moved by changing the angle of the steering mirror.

In another aspect, a system is designed such that a single mirror placed in the optical system will primarily tune the chief ray of the output beam while a second mirror is used to control the beam location.

In another aspect, a technique is provided for using the output tapped from the reciprocal path of the optical system to generate a time varying measure of optical intensity which can be correlated with beam position to form an image of retroreflectivity on the biosensor chip surface.

In another aspect, a means is provided to calculate the relative change in sensor resonance peak location during successive scans with the aid of a wavelength reference such as a fiber optic, Fabry-Perot etalon, which is used to correct for laser velocity variations with a wavelength sweep and between sweeps.

In another aspect, a method is provided to capture more than one resonance peak location in the sensor spectrum which are averaged together to reduce noise present in individual peak measurement.

In another aspect, a ring resonator is formed from silicon waveguides and which has formed on the surface of a thin layer of silicon dioxide where the layer of silicon dioxide is thin compared to the evanescent field of the silicon waveguide, and where a layer of silane linking molecules are covalently bound to the silicon dioxide layer.

In another aspect, two or more rings are exposed to a test fluid where at least one is clad with a material of thickness substantially greater than the length of the evanescent field, and where at least one is exposed to the test fluid and where the relative change between these two classes of rings is used as the output signal of the system.

In another aspect, a biosensor chip is provided to include grating couplers and optical sensors where the grating couplers are offset from the optical sensors by a certain distance and were the grating couplers are arranged to be optically visible from a scanning system while the optical sensors are embedded in a flow channel that this laterally displaced and which need not be optically accessible.

In another aspect, a uniquely identifiable pattern is placed in proximity to a grating coupler so that each ring can be uniquely identified by decoding the adjacent pattern.

In another aspect, a means is provided to route an optical waveguide underneath a flow channel by placing an upper cladding material on the waveguide in the region of the flow channel.

In another aspect, a means is provided to localize biological spotting of an optical ring resonator by placing a hydrophobic film in the areas surrounding the ring resonator, and by coating the ring surface with a hydrophilic material, such as silicon dioxide, thus providing an area where an aqueous droplet will be trapped.

In another aspect, a transition is provided between a clad waveguide and an unclad waveguide where the unclad waveguide is coated with water and where the cladding is constructed from CYTOP.

In another aspect, a cladding is placed on an optical waveguide which is simultaneously refractive index matched with water and resistant to chemical activity with components in the water and where a transition between a clad portion of the waveguide and an unclad portion exists where the unclad portion is coated with and aqueous solution and contains surface chemistry reactive to components in the aqueous solution.

In another aspect, a biosensor platform is provided to include a chip comprising a plurality of ring resonators spread across a plurality of flow channels where said rings are sequentially addressed using steered mirrors and interrogated with a tunable laser and an external wavelength referencing system where the referencing system is used to determine the relative frequency shift of each sensor and control ring at periodic intervals.

In another aspect, a method is provided for focusing on a fraction of a highly angled surface (a surface where the simply reflected signal will not return to the optical system) by rastering a laser beam over the field of view and reconstructing an image of retroreflective structures comprising grating coupler loops or retroreflective grating gratings, and repeating this at a variety of focal distances until the retroreflective signal is maximized.

In another aspect, a method is provided for identifying a particular grating coupler loop by placing a retroreflective grating in proximity to the grating couplers, and where a distinctive pattern of the retroreflective grating can be used to uniquely identify a particular grating coupler from within an array of grating couplers.

In another aspect, a method is provided for maintaining alignment of an array of optical spot positions held by a rastering system with an array of grating couplers by intentionally offsetting the location of the spot in a predetermined pattern on each subsequent visit to a particular grating coupler, and by using the power fluctuations seen between the pattern created by each subsequent visit to calculate the direction of misalignment, which will be used to re-determine the location of that individual spot.

In yet another aspect, a method is provided for tuning the chief ray of the scanning system by varying the setting of one mirror, designed to primarily affect chief ray and completing a scan by a second mirrors, designed to primarily affect spot location, and performing this activity iteratively until optical efficiency of the biosensor coupling is optimized.

These and other aspects, and their implementations are described in detail in the drawings, the description and the claims.

BRIEF DESCRIPTION OF THE DRAWINGS

FIG. 9 shows an exemplary process for focusing a probe beam onto a biosensor chip in the apparatus in FIG. 1.

FIG. 10 shows an exemplary process for registering on-chip biosensors on a biosensor chip in the apparatus in FIG. 1.

FIGS. 11, 12 and 13 illustrate operations of on-chip identification markers for identifying different biosensors on a biosensor chip in the apparatus in FIG. 1.

FIG. 14 shows an exemplary process for adjusting the registration of biosensors on a biosensor chip in the apparatus in FIG. 1.

DETAILED DESCRIPTION

Figure 1:
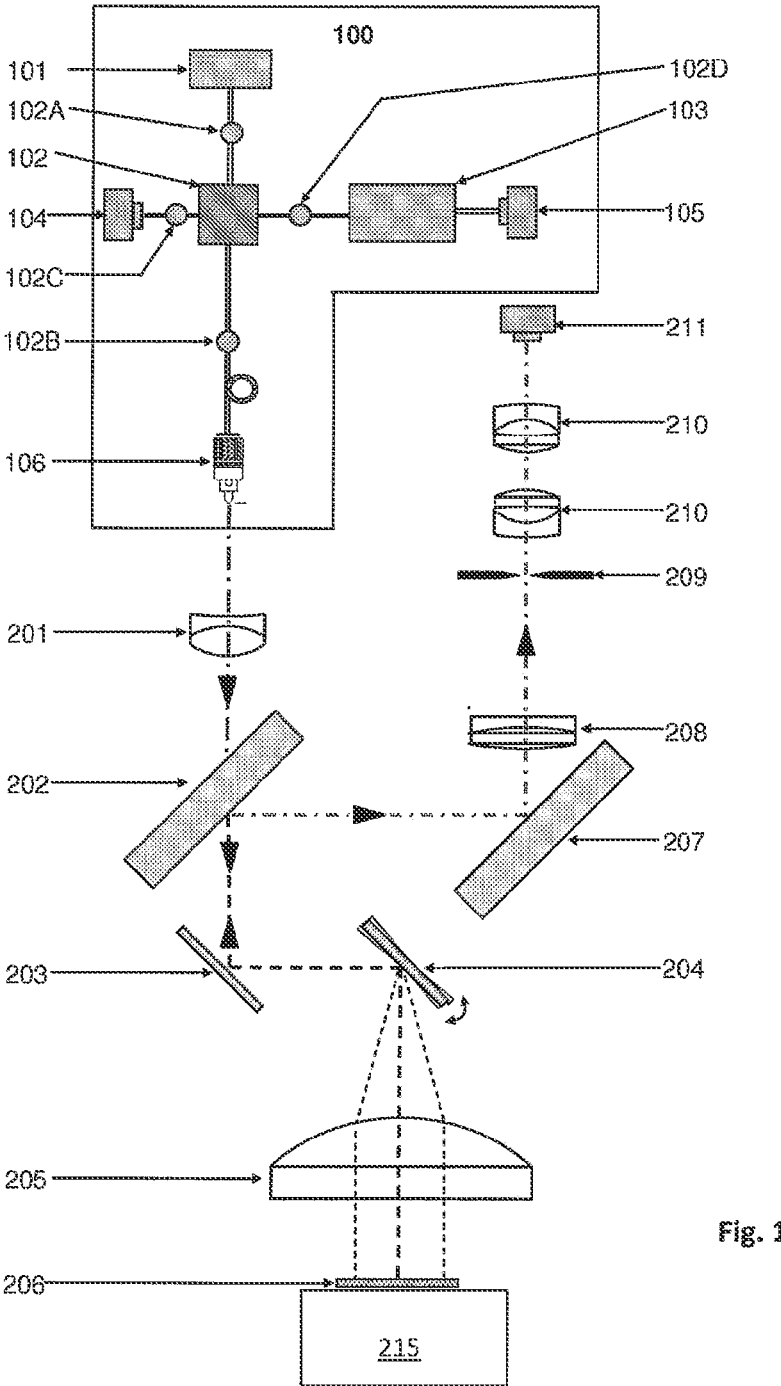
FIG. 1 shows one exemplary implementation of a biosensor apparatus based on optical probing and sensing.

Apparatus, sensor chips and techniques for optical sensing of substances by using optical sensors on sensor chips described in this document use free space to direct probe light onto a sensor chip and to receive returned probe light from the sensor chip via free space for further detection and processing. Examples of sensing apparatus described here can be used to identify and spectrally interrogate resonant cavity optical biosensors fabricated a substrate or chip, e.g., a silicon chip. In one implementation of the apparatus, light from a narrow line-width, tunable laser is sourced via an optical fiber system to a free-space optical system that shapes, guides and focuses the beam onto the biosensor chip. The apparatus can be structured to perform fast and efficient mode alignment between the free-space beam and on-chip optical input and output optical couplers, e.g., grating couplers, which in turn couple light into and out of optical waveguides on the bio sensor chip. While grating couplers are described as the exemplary implementations of optical couplers in the examples in this document, other optical coupling mechanisms, including edge coupling, taper coupling, or prism coupling, can also be used for input and output optical coupling on a sensor chip. Light is routed to on-chip optical biosensors via these waveguides. Each on-chip biosensor reacts or responds to changes in ambient optical properties due to presence of relevant biomolecules. Sensor response is obtained by interrogation with a wavelength sweep of the tunable laser that sweeps or tunes the laser wavelength through different wavelengths with a spectral range and by capturing the light after propagation through the sensor. Note that in the case of ring resonator sensors, when the light is off-resonance, the light is primarily coupled weakly to the sensor, and passes strongly through the sensor when the light is on resonance.

The free-space optical system can be implemented to include co-propagating forward and reverse light paths. The forward path propagates the beam through multiple optical components which shape and focus the beam onto the chip via on-chip optical input couplers. The laser is then operated to perform a wavelength sweep to measure the frequency response of the biosensor. The width of the wavelength sweep will span at least one resonant frequency. Other options are to span at least one free spectral range of the sensor, or to span a larger number of resonances. The presence of biomolecules on a biosensor on the chip causes an optical response of the biosensor to change in comparison with the optical response of the biosensor in absence of the biomolecules in response to the spectral sweep based on the physical properties and chemical composition of the deposited molecules. This response is exhibited as a change in the intensity of light passing through the sensor as a function of wavelength and captured at a photodetector at the end of the reverse optical path. Light is routed to and from the sensor via optical waveguides which terminate at input and output grating couplers located at either end. Grating couplers transform a planar propagating mode into a free-space optical beam and vice versa.

The optical fiber system comprises single-mode or polarization maintaining (PM) optical fibers, optical fiber splitters, a wavelength referencing system as well as a retro imaging system used to locate biosensors on the chip.

To identify sensor locations on the chip, the optical beam emerging from the forward path of the instrument is set to raster the chip surface to measure a spatial map or image of optical responses from the chip at different locations on the chip. This map or image of the chip is formed by capturing the reflections from the surface at a photodetector. With the knowledge of coupler locations, multiple sensors are interrogated at high speeds by successively returning to these locations.

FIG. 1 shows one exemplary implementation of a biosensor apparatus based on optical probing and sensing. This apparatus includes an optical interrogator (100, 200) and a chip platform (215) for holding one or more biosensor chips (206) under measurement. The optical interrogator includes a fiber optic system (100) and a free-space optical system (200) that collectively direct probe light to a biosensor chip (206) and collect and measure returned probe light from the biosensor chip (206). The relative position between the chip platform and the optical interrogator can be controlled and adjusted by using a positioning system, e.g., a mechanical positioning stage having one or more motion actuators.

The fiber optic system (100) is an implementation of an optical subsystem that provides a wavelength-tunable laser (101) for generating the probe light to be delivered to the biosensor chip (206) for optically interrogating on-chip biosensors, a wavelength reference that calibrates and measures values of wavelengths of the probe light when the wavelength of the laser (101) is swept, and a spatial registration of on-chip optical identification markers for providing on-chip position reference. This optical subsystem (100) can also be implemented by using discrete optical components or a combination of discrete optical components and fiber optics. For example, a fiber etalon can be replaced by a free-space etalon. For another example, a free-space laser and free space splitters can be used to eliminate the corresponding fiber components.

In the specific example shown in FIG. 1, the fiber optic system (100) uses a 2×2 fiber optic beam splitter (102) to direct the probe light for optically interrogating the biosensor chip (206) and for providing the wavelength reference, and to direct returned probe light from the biosensor chip (206) for the spatial registration of the on-chip identification markers. The 2×2 fiber optic beam splitter (102) includes four splitter ports of port 1 (102A), port 2 (102B), port 3 (102C) and port 4 (102D) to direct light via fibers. Light from the tunable laser (101) to the beam splitter (102) is sourced through splitter port 1 (102A) which is subsequently split into two paths: a first path via port 2 (102B) to a fiber collimator 106 feeding an collimator (201) of the free-space optical system (200) and a second path via port 4 (102D) to a wavelength referencing system (103) and a wavelength referencing optical detector (105). The port 2 (102B), in addition for directing probe light to the free-space optical system (200) and the biosensor chip (206), is also used to collect returned probe light from the biosensor chip (206) via the free optical system (200). The collected returned probe light is routed to port 3 (102C) and is received by a photo-detector (104) to produce an image of the biosensor chip (206) that includes images of the on-chip identification markers.

In the free-space optical system (200), the collimated beam of probe light from the collimator 106 of the fiber optical system (100) is received by a free space collimator 201 and propagates through a free-space beam splitter (202) to impinge on a first motorized tip-tilt scanning mirror (203). The scanning mirror (203) reflects the collimated beam to a second tip-tilt scanning mirror (204) to reach an objective lens (205), which converges the beam onto its focal plane where the biosensor chip (206) is placed. In on implementation, each of the two scanning mirrors (203, 204) can be controlled by at least one actuator to tilt the mirror to rotate around two orthogonal axes X and Y under two control voltages. The control voltages on the two scanning mirrors (203, 204) can be calibrated to represent beam positions and chief-ray angles on the surface of the biosensor chip (206).

As illustrated, the objective lens (205), the scanning mirrors (204, 203) and the beam splitter (202) also collect returned light from the biosensor chip (206). The beam splitter (202) splits the collected returned light from the biosensor chip (206) into a first collected optical signal that is directed back to the photo-detector (104) of the fiber optical system (100) to produce a raw image of the biosensor chip (206), and a second collected optical signal as a sensor optical signal that is directed into an optical sensing module having an optical detector (211) in the free optical system (200) that receives and detects the sensor optical signal for measuring biomolecules present at the biosensors on the biosensor chip (206).

Figure 2:
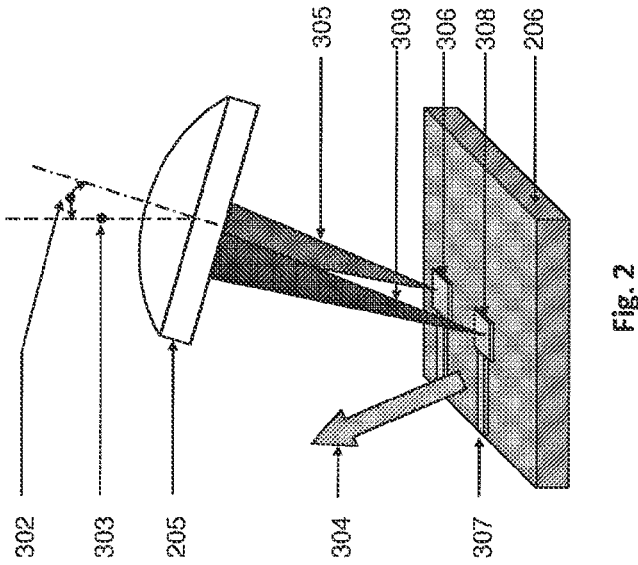

FIG. 2 shows a part of the biosensor chip (206) and the objective lens (205) of the free optical system (200) to illustrate coupling probe light on to the biosensor chip (206) and collecting light from the biosensor chip (206). The biosensor chip (206) has one or more optical input coupling structures (306) that couple probe light from the objective lens (205) into the biosensor chip (206) and one or more output coupling structures (308) that couples light out of the biosensor chip (206). An optical input coupler (306) converts the probe light from the free-space beam into a guided wave through an on-chip optical waveguide (307) which routes the probe light to one or more on-chip biosensors. An optical output coupler (308) performs a reciprocal transformation of light by converting light in an on-chip waveguide (307) into a free-space beam (309) that is at a direction different from a direction of the specular reflection of the input beam off of the input coupler. For example, each optical output coupling structure (308) can be configured to make light emerging from the chip at an angle that matches the angle of incidence of the forward path. Under this configuration, the light emerging from the chip traces a reciprocal path arriving at the free-space beam splitter.

The above design of coupling light from the chip at a direction different from the specular reflection of the input light allows for separation of the specular reflection of the input light at the chip surface and the output light produced by the one or more optical output coupling structures (308) to prevent the specular reflection from entering the optical detector (211) in the free optical system (200) that receives and detects the sensor optical signal for measuring biomolecules. To achieve this, the chip (206) and the free-space optical system (200) are mounted at an angle to each other, such that the majority of the specular reflected light falls outside of the collection aperture of the objective lens (205). In FIG. 2, the objective lens (205) is mounted at an angle (302) from the surface normal (303) of the chip (206). The objective lens (205) is positioned to receive the output light from an output coupling structure (308) while the specular reflection (304) from the chip (206) is shown to escape the numerical aperture of the objective lens (205). The coupling structures (306, 308) can be implemented in various configurations. In the examples described below, grating couplers are used to implement the input and output coupling structures (306, 308). In some implementations, an input coupling structure can also be operated as the output coupling structure, although this will require repositioning of the spatial filter (209).

When the image of the chip is created by raster, light from specialized retroreflective gratings is reflected at the same angle as the angle of incidence. This light is collected by the objective lens (205) and traces a reciprocal path through the free-space optical system (200) and couples back into the collimated end of the fiber optic beam splitter and emerges at s at port 3 (102C). The photo-detector (104) is provided to receive light output from the port 3 (102C) and produces an electrical signal captured by appropriate instrumentation. The collected data is then transformed into a 2-D image and automated software uniquely identifies the location of coupling structures and uniquely identifies the couplers with the aid of pre-set retroreflective gratings.

The mode of a grating coupler can be approximately matched to that of a single mode (SM) or polarization maintaining (PM) optical fiber. The lens combination used in the free-space optical system is selected to meet the requirements of mode matching between free-space and optical fiber. In one implementation, the second scanning mirror (204) is mounted at the front focal length of the objective lens (205) in order to minimize the deviation of chief ray angle in cases of off-axis incidence—as the second scanning mirror (204) is tilted from its nominal position. Additionally, the first scanning mirror (203) allows for correction of misalignment errors caused by component variability, machining tolerances and errors imparted during assembly. In particular, angular or translational misalignments may cause the chief ray angle, wave-front error, spot diameter, spot spatial profile, etc. to deviate from their optimal/ nominal settings, in which case, the first scanning mirror can be biased around its pivot point to offset the effect of such errors.

In operation, the scanning mirrors (203, 204) are used to raster the beam of the probe light from the free space optical system (200) onto the chip (206). The beam spot dwells on a grating coupler for the duration of a wavelength sweep through a selected spectral range, before translating onto the next coupler. FIG. 2 illustrates this operation. As the spot (305) dwells on the input coupler (306), light from free-space beam is transformed into a guided wave mode which propagates through the chip via waveguides (307) before emerging from the output coupling structure (308). At the output, the reciprocal transformation from a guided-wave mode to a free-space mode is achieved (309). As light emerges from the chip, its angle matches the angle of incidence of the forward path and it traces a reciprocal path arriving at the free-space beam splitter (202) shown in FIG. 1.

Figure 3:
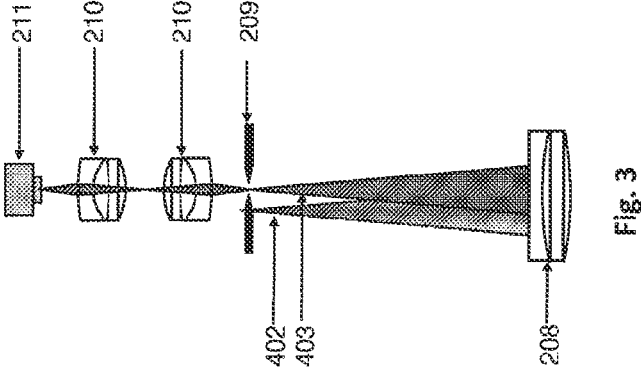
FIGS. 2 and 3 illustrate operations of the apparatus in FIG. 1.

FIGS. 1 and 3 also illustrate the structure and operation of the optical sensing module having the optical detector (211) in the free optical system (200). The optical sensing module in this example includes a fold mirror (207) which directs the beam received from the beam splitter (202) through an imaging lens (208) whose focal plane is spatially filtered using a spatial filter (209) which may be a knife-edge, or a pin-hole. Such an arrangement transmits light along the direction of light coupled out by the output grating coupler (308) and blocks the unwanted light diffracted by the input coupler (306) that is collected by the objective lens (205) and contributes to noise at the detector (211). The pinhole (209) relies on the spatial separation between the spots formed by undesired diffracted beam emerging from the input coupler (306) and the signal beam emerging from the output coupler. As illustrated in FIG. 3, a slow imaging lens (208) with a long focal length can be used to amplify this separation at the expense of increasing the spot size. A lens offering on-axis diffraction limited performance can sufficiently isolate the two spots (402) and (403) such that the noise spot is successfully blocked by the pinhole (209). The signal detector (211) is placed at the image plane of a relay lens system (210).

Note that there are a variety of other spatial filter mechanisms well known to those skilled in the art of optical system design, and that these filters can be substituted for the pin-hole and relay lens system described as the preferred embodiment.

During a wavelength sweep, biomolecules immobilized on the surface of an on-chip biosensor alter the resonant wavelength which results in a change in intensity as a function of wavelength as the laser is tuned over the resonant wavelength.

The apparatus performs a wavelength sweep of the biosensor and the wavelength reference simultaneously. For example, an on-chip biosensor can include a resonant optical cavity such as formed by a waveguide patterned in the shape of a ring accessed through linear waveguides terminated at either end by grating couplers. Various wavelength references can be used to implement the reference (103) and one such example is a fiber optic, Fabry-Perot etalon with known optical properties, such as free spectral range (FSR), finesse and transmittance.

During each wavelength sweep, resonance location of the sensor cavity is determined by observing the sensor transmission spectrum. The spectrum exhibits maximum transmission when the laser is off-resonance, and follows a Lorentzian line-shape decline when the laser wavelength approaches the resonance wavelength of the cavity. As biomolecules bind or un-bind from the sensor, its spectrum is changed, such that the resonance wavelengths are red shifted (in case of binding) or blue shifted (in case of depletion), as a function of the mass, size, and conformational shape of the molecule. This shift is observed during successive wavelength sweeps and is the key measurement of the biosensing apparatus. It is therefore important to eliminate noise sources which cause erroneous movement of sensor resonance peaks. To accurately measure sensor peak locations, etalon peaks are used as a reference. Light propagating through the etalon experiences the same wavelength sweep creating a Fabry-Perot cavity spectrum at the photodetector. Since both the sensor cavity and the etalon are addressed and sampled near simultaneously, return signals from these devices are well aligned in time and wavelength.

In FIG. 1, a detection processing unit is provided to receive signals from the detectors 104, 105 and 211 and to process these signals. The detection processing unit may be programmed by automated software which detects the location of resonance peaks of the sensor cavity as well as the location of peaks in the etalon spectrum. As mentioned, the FSR of the etalon is known and under controlled conditions, is assumed to be a constant. The software determines important properties of the resonance line-shape including; location, the Quality Factor (Q), extinction ratio (ER), left and right wall slopes, peak transmission, and nature the of the peak, such as linear, split and non-linear etc. The detection processing unit can also be used to determine the locations of all peaks present in the etalon spectrum. To make an accurate measurement of sensor resonance peak location, the two spectrums (sensor and etalon) are overlaid. In addition to the detection processing unit, a controller unit can also be provided to control operations of various components and to coordinate operations of various components. For example, the synchronization of the scanning of the probe light on a sensor chip and the scanning of the tunable laser and other control operations can be implemented in the controller unit. In some implementations, the controller unit may be a separate unit form the detection processing and receives outputs from the detection processing unit and uses such outputs in carrying out its control operations. In other implementations, the controller unit may be integrated with the detection processing unit as a single unit. A computer or microprocessor can be used as part of the controller unit.

In one implementation of the design in FIG. 1, the FSR of the etalon can be set to be smaller than the FSR of the sensor cavity, resulting in numerous etalon peaks overlaid with a few sensor peaks. The algorithm references the resonance peak to the surrounding etalon peaks such that a proportional distance from either the left or the right surrounding peak is calculated, assuming that the distance between etalon peaks is constant. Subsequently, the number of etalon peaks from the beginning to the one adjacent to the left resonance peak are counted and multiplied to the etalon FSR. These two quantities are added to produce the exact location of a sensor peak. This method eliminates the inaccuracy caused by the variation in laser sweep velocity. To further improve the measurement accuracy of wavelength peak locations, a wide wavelength sweep encompassing multiple sensor resonances can be used. Each peak location is identified in a manner described above and then averaged to produce a less noisy result.

In implementing the biosensor apparatus in FIG. 1, biosensors on the biosensor chip (206) can be implemented in various configurations. As a specific example, ring resonators can be implemented as on-chip biosensors on the biosensor chip (206) in FIG. 1.

Figure 4:
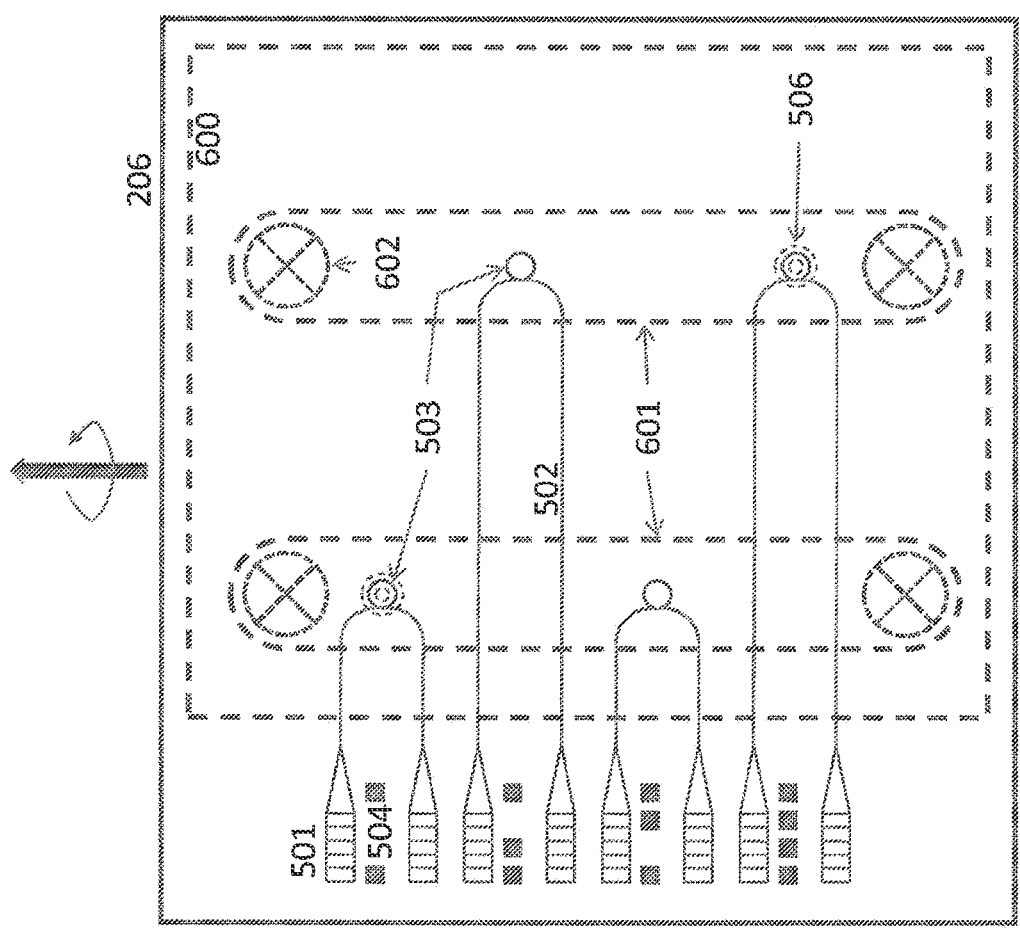
FIGS. 4, 5, 6, 7a and 7b show exemplary features in a biosensor chip in FIG. 1.

FIG. 4 shows an example of a biosensor chip (206) that includes ring resonators 503 addressed by waveguides 502. Light is coupled into/out of the chip using grating couplers 501. The chip in this example is designed to have multiple flow channels 601 where fluid is directed across the chip. One option is to construct a gasket 600 which has the flow channels 601 cut into the gasket 600. Fluid can enter and leave the flow channel through ports 602.

The chip surface is coated in large part with a cladding material which serves to prevent contact between the waveguides 502 and either the gasket or the fluid or components of the fluid except where desired. For example, the waveguides passing under the flow channel nearest to the grating couplers and proceeding to the far flow channel should not have any interaction with the fluid in the near flow channel, and this should be clad in this region. Additionally, the gasket material could interact with the waveguides, and as such the waveguides underneath the footprint of the gasket should be clad as well. In areas where it is desired to have interaction between the fluid or elements in the fluid and the waveguides, such as on all or part of the rings, then the cladding material can be removed at a ring resonator 106, such as by lithographic processes, to expose all or part of the ring resonator 106 for interaction. Also note that not every ring need have the cladding removed. Certain rings can have the cladding remaining intact, such that they may be used as reference ring resonators, rather than working biosensors, for controls in order to remove effects such as temperature from the sensor output and thus calibrate the system.

Additionally, it is desired that the identity of each ring be unambiguously determined. The chip may include multiple biosensors and a unique identifier 504 can be placed in proximity to each grating coupler, and constructed so that it can be scanned by the optical system. This unique identifier could be a binary code, as pictured, or any other type of physical encoding scheme. In this example, each ring resonator 503 is optically coupled to a respective waveguide 502 and two grating couplers 501 are coupled at two ends of the waveguide 502. Optical identification marks 504 are formed adjacent to respective grating couplers 501 to provide location identification for the respective adjacent grating couplers 501.

In order to couple more efficiently into grating couplers, and to prevent reflections, it is desired to couple into the chip at an angle about the rotation axis shown in FIG. 4.

Figure 5:
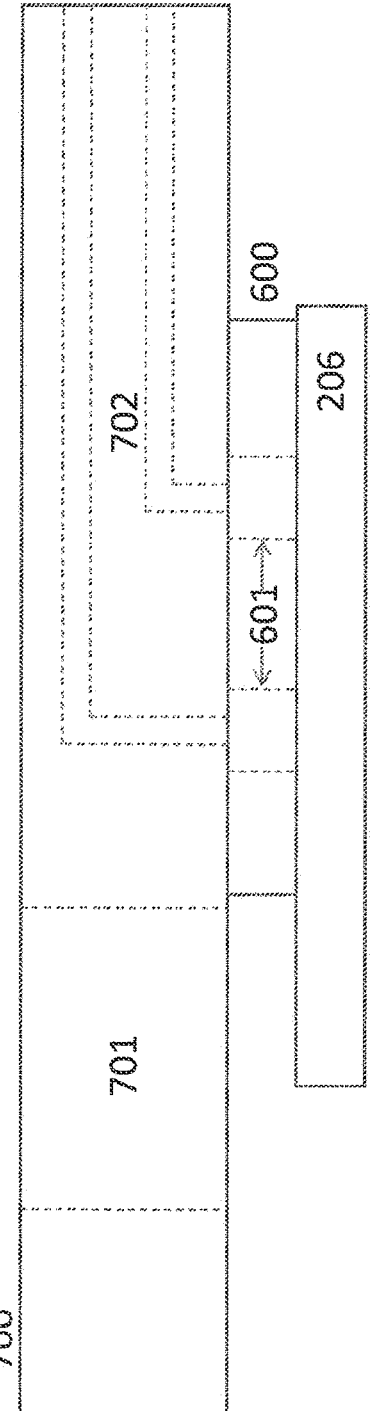

FIG. 5 shows a cross-section of an exemplary embodiment of the invention where a gasket 600 containing flow channels 601 is placed between the chip 206 and a fluidic manifold 700 which contains channels 702 through which the fluid can enter and exit the flow channels 601. A seal is made with the gasket by placing a compressive force between the chip 206 and the manifold 700. Note that both the gasket 600 and the manifold 700 are removed or do not extend to the area over the grating couplers, such that the optical system can interrogate the grating couplers without interference.

An alternative embodiment would be to construct the flow channels monolithically in the gasket, or have the gasket permanently bonded to the manifold, such that compression is not required to form the upper seal between the gasket and the manifold.

Figure 6:
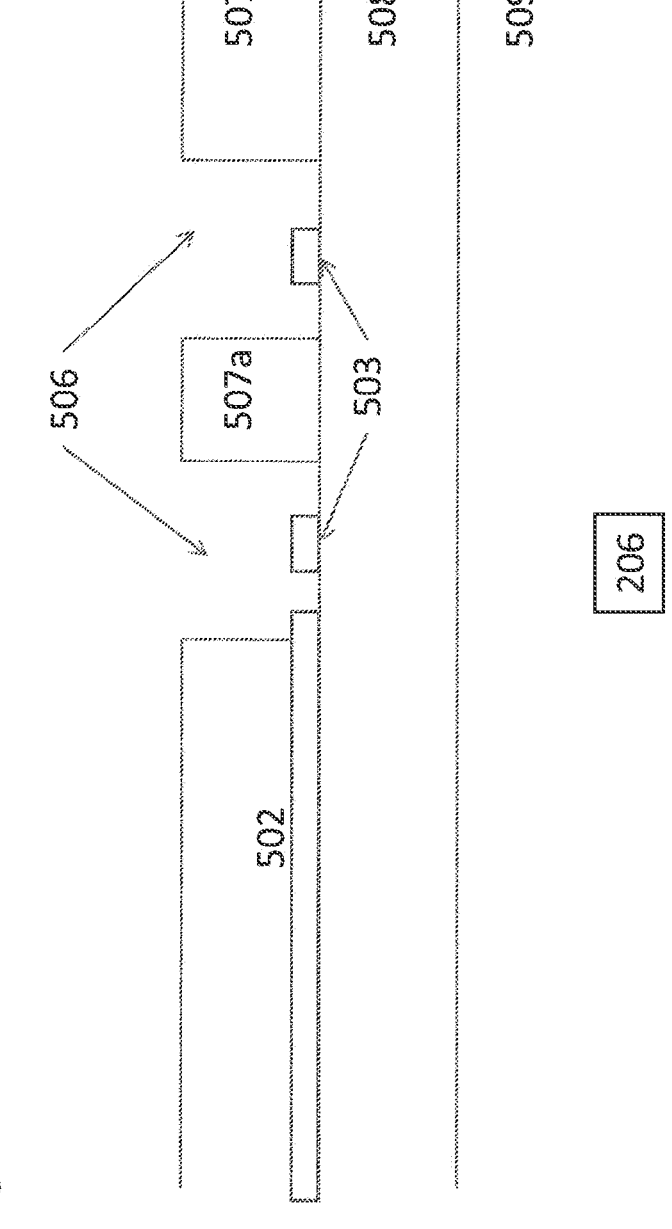

FIG. 6 shows a cross-section of a ring sensor 503 and the input waveguide 502. The cladding 507 covers the input waveguide 502, but has been removed from the area 506 over the ring sensor 503. In this example, a central island 507a is optionally formed in the center of the ring sensor 503. Both the upper cladding 507 and the lower cladding 508 have a refractive index less than that of the waveguide 502 in order to maintain proper optical waveguiding operation. An example material system for this is waveguides constructed from silicon and the lower cladding formed from a buried oxide of a silicon-on-insulator wafer. In this example, the substrate 509 is a silicon handle wafer. Note that as the light travels down the waveguide, it passes the boundary from where an upper cladding is present and where the upper cladding is removed. One way to reduce or eliminate the reflections associated with this boundary is to provide an index match between the upper cladding 107 and the fluid to be introduced to the sensor. The cladding material should be mostly non-reactive with the material to be sensed, of which the fluid is comprised. In certain circumstances, it may be advantageous to have the majority of the sensor chip be hydrophobic while creating a hydrophilic region in the exposed areas 506. Taking all of these considerations into account, an optimal choice of material for the upper cladding 507 is often from the class of polymers comprising fluoro-polymers or perfluoro polymers. The presence of the fluorine can be used to lower the refractive index to be similar to that of water, about 1.33, and also serves to form a hydrophobic and largely non-reactive surface. A particularly good example of such a polymer is CYTOP, which has an index of refraction of 1.33 and is inert and hydrophobic, and which is readily patterned through a lithographic etching process.

Figures 7A, 7B:
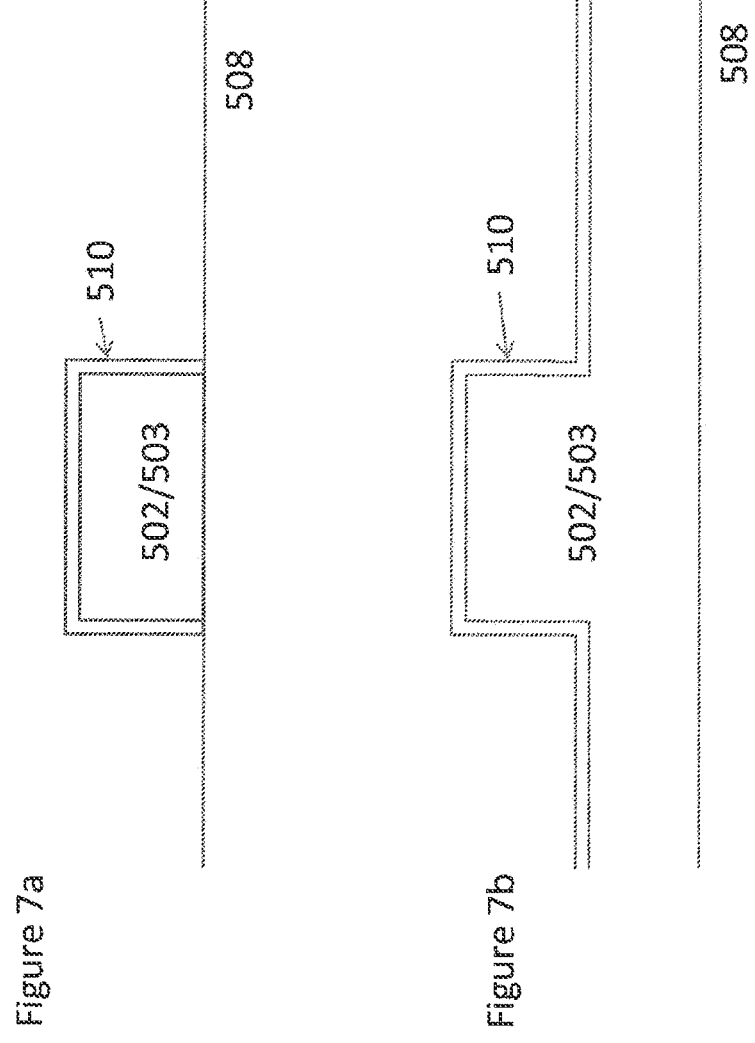

FIGS. 6a and 6b show a method for attaching probe molecules to the sensor surface. The silicon waveguide 502 is formed into a ring 503 and coated with a thin layer of silicon dioxide 510. This thin layer of silicon dioxide 510 allows the evanescent field to still strongly react with any chemistry placed on top, but also serves as a common way to initiate surface binding via a class of molecules known as silanes, which bond covalently with glass. Two different types of common waveguides are shown, in FIG. 7 a, a completely etched waveguide 502 which exposes the lower cladding 508, and in FIG. 7 b, a partially etched waveguide 502 is shown where the lower cladding 508 is not revealed.

Figure 8:
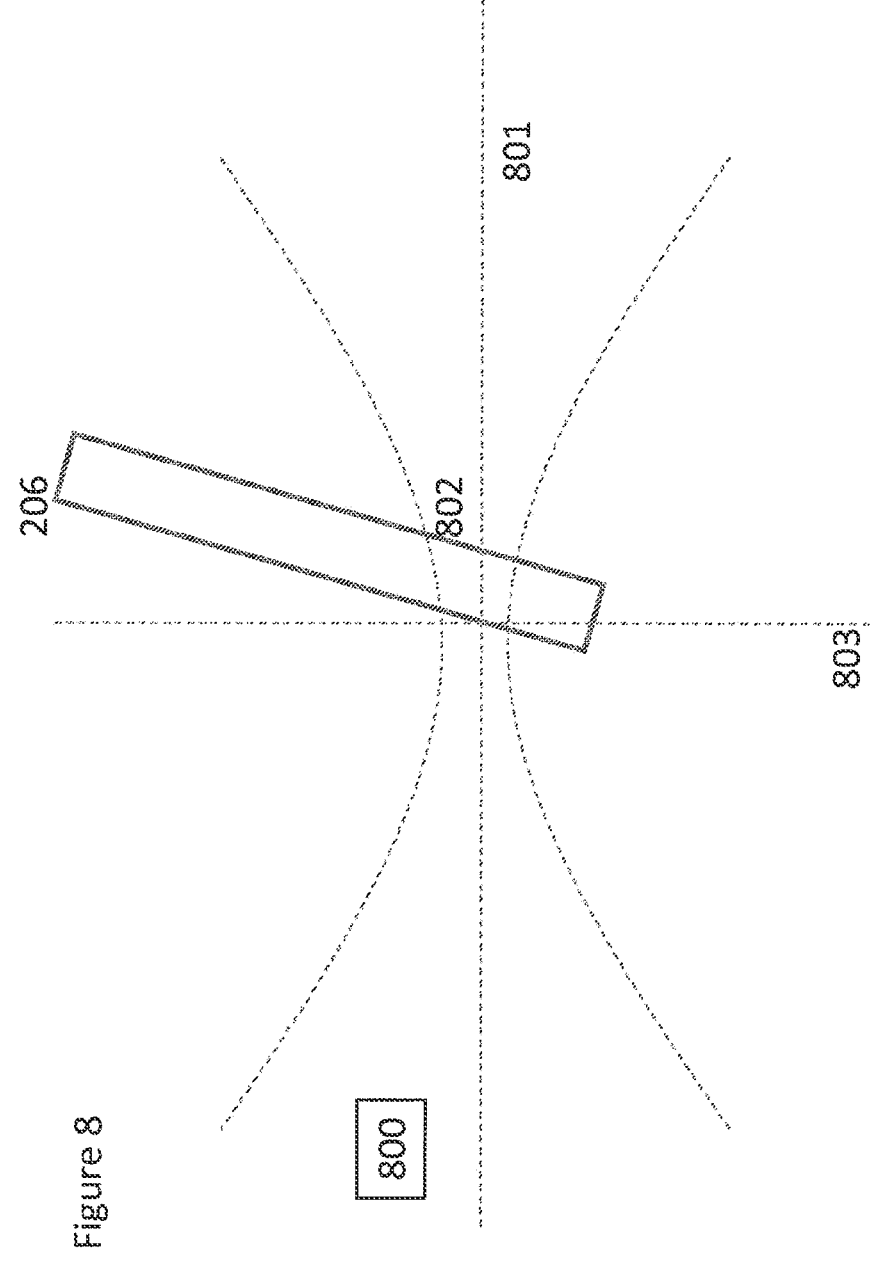
FIG. 8 illustrates a focusing operation of the apparatus in FIG. 1.

FIG. 8 shows a diagram of the chip 206 as placed in the optical field 800 of the free space optical system (200) containing focusing optics in FIG. 1. The chief ray of the beam 801 is not normal of the surface of the chip 206. In this example, the focal plane 803 does not include the entirety of the chip surface of the chip 206. The chip 206 is shown rotated about the axis indicated in FIG. 4. As such, it is important to locate all grating couplers 501 and identification marks 504 within a line on the chip surface so that they may all be viewed from a constant focal setting of the system.

Referring to FIGS. 1 and 2, the probe light from the free space optical system 200 is directed through the air onto grating couplers for ring resonators on the chip. For light to be efficiently coupled into grating couplers, the spot size of the light should be approximately the same size as the grating coupler. To achieve proper spot size the free space optical system 200 is designed to focus the beam on the chip surface. Since all light paths internal to the optical interrogator have a fixed path length, the path between the optical interrogator and chip surface can be adjusted to achieve the desired beam focusing on the chip surface.

The distance between the optical interrogator and the chip surface can be referred to as the focus height. In one implementation, adjusting the focus height is achieved via a mechanical stage. The stage is moved via automated (software controlled) actuator. The spot of light is positioned near a grating coupler and is rastered through different grating couplers at different locations on the chip to form an image of the grating couplers on the chip. During the rastering, the maximum intensity of the light coming out of the output grating coupler is measured and stored in memory. Once one raster is complete and the intensity of light emitted on the output coupler is recorded, the actuated stage is moved "X" microns and the process is repeated. If the measured light emitted is greater than the previous iteration, the direction and amplitude remain substantially unchanged and the stage is moved again by the same amount and the process is repeated. If the measured light response is less than that of the prior iteration, the actuated stage movement is reduced by approximately one half and the direction is reversed and the process is repeated. This process is repeated until the run to run variation has converged below a certain percentage or threshold. FIG. 9 is a flow chart illustrating the above focusing adjustment.

An alternative embodiment would be to substitute other algorithms, such as a binary search, for the simple step and repeat algorithm described above.

By design, all sensors on the chip have roughly the same focus distance. So by choosing one sensor and focusing the beam on that particular sensor, all other sensors will come into focus. Also inherent in the system design is the fact that the when a grating coupler comes into focus, its neighboring retroreflective gratings come into focus. Once the chip has been placed in focus of the optical interrogator, the chip is ready for the next step which is sensor registration.

In various sensing applications using the biosensor apparatus in FIG. 1, each sensor on a chip can have a unique role in testing and different sensors on the chip are used to perform different measurements. In such applications, different sensors on the chip need to be separated and identified by assigning a unique identity to each sensor. In order to assign a unique ID to each sensor, the chip can be "registered" by the optical interrogator by performing an optical raster scanning over the chip for registration before a sensing raster scanning is performed for obtain actual measurements from the sensors.

FIG. 10 shows an example of a chip registration process for assigning an identification number to each individual sensor on the chip. As shown in the example in FIG. 4, ID numbers can be etched on the chip next to respective on-chip sensors in the form of optical identification marks 504, such as retroreflective gratings. The retroreflective gratings are reflective structures patterned in a binary sequence and each set of retroreflective gratings, 504, comprises a binary number that is a unique identification number of its' respective sensor. The process of "registration" is done by taking a "picture" of the chip, finding each sensor, and then reading its corresponding retroreflective grating structures. Obtaining the "picture" of the chip is done by "rastering" the entire chip surface. Rastering refers to scanning back and forth over the entire chip surface with a focused spot. Rastering is accomplished by driving an automated 2-axis mirror and steering the spot over the chip. During the rastering step, reflected/emitted light is collected at two different places in the optical interrogator via photo-detectors and a set of analog-to-digital converters (ADCs). The sampling of these signals is synchronized in time with the generated mirror steering DAC signals. The collected signals can be reconstructed to create 2D images of the chip.

Figure 11:
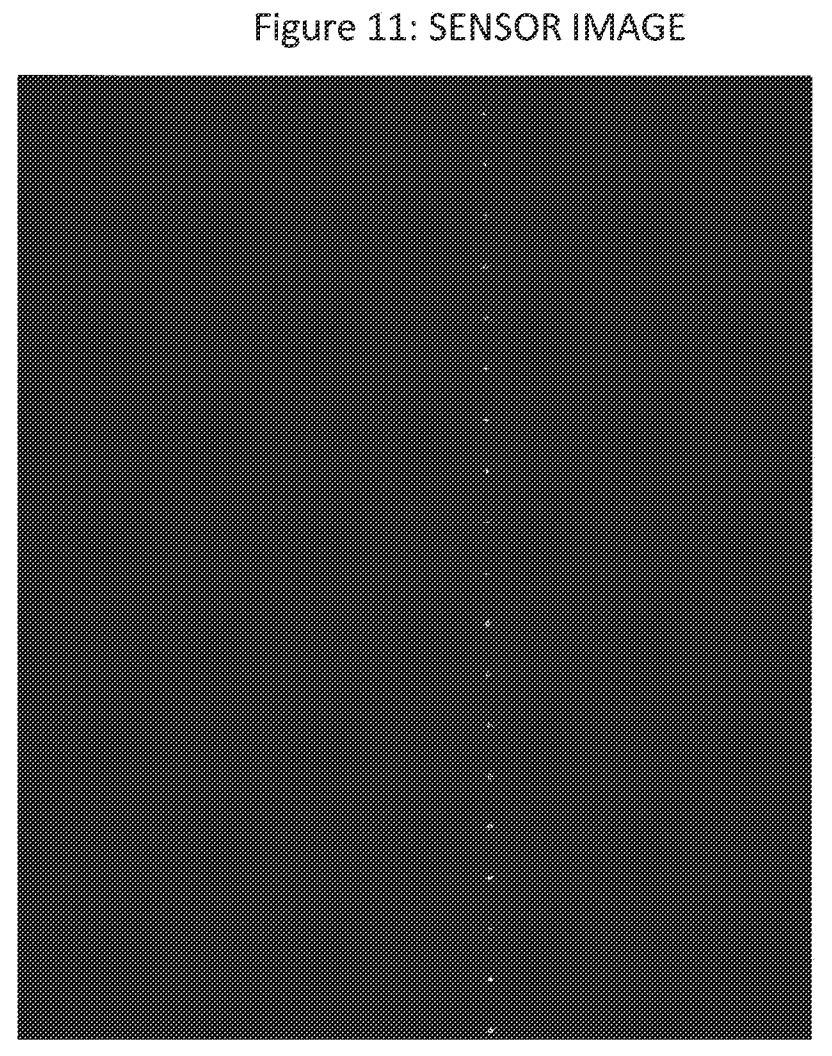

The first of the two collected signals is the "sensor" signal which is collected by the photo detector 211 and is used not only during registration, but also during focusing and measurement phases of instrument use. In the context of registration and sensor identification, this signal is used to locate where on the chip each sensor resides. The location of each sensor is defined by the mirror voltages required to move the spot on top of the input grating coupler associated with that particular sensor. These sensor location voltages are found by doing a lookup of the reconstructed picture that the signal detector generated. The picture of the chip that is generated by the signal detector is analogous to stars in the night sky. Most of the image is dark but where a sensor exists, there is a bright spot. FIG. 11 shows an example of such an image of identification marks on a chip obtained by the detector 211. Because the sample number of the bright spot is known and the sensor signal detector sampling is time synchronized with the mirror driver signals, the mirror driver voltages that brought the mirror to that sensor can be inferred. At this point in the registration process the mirror voltages that drive the spot to each sensor input grating coupler are known. These will be used later to decide where the retroreflective grating signals should be located.

Figure 12:
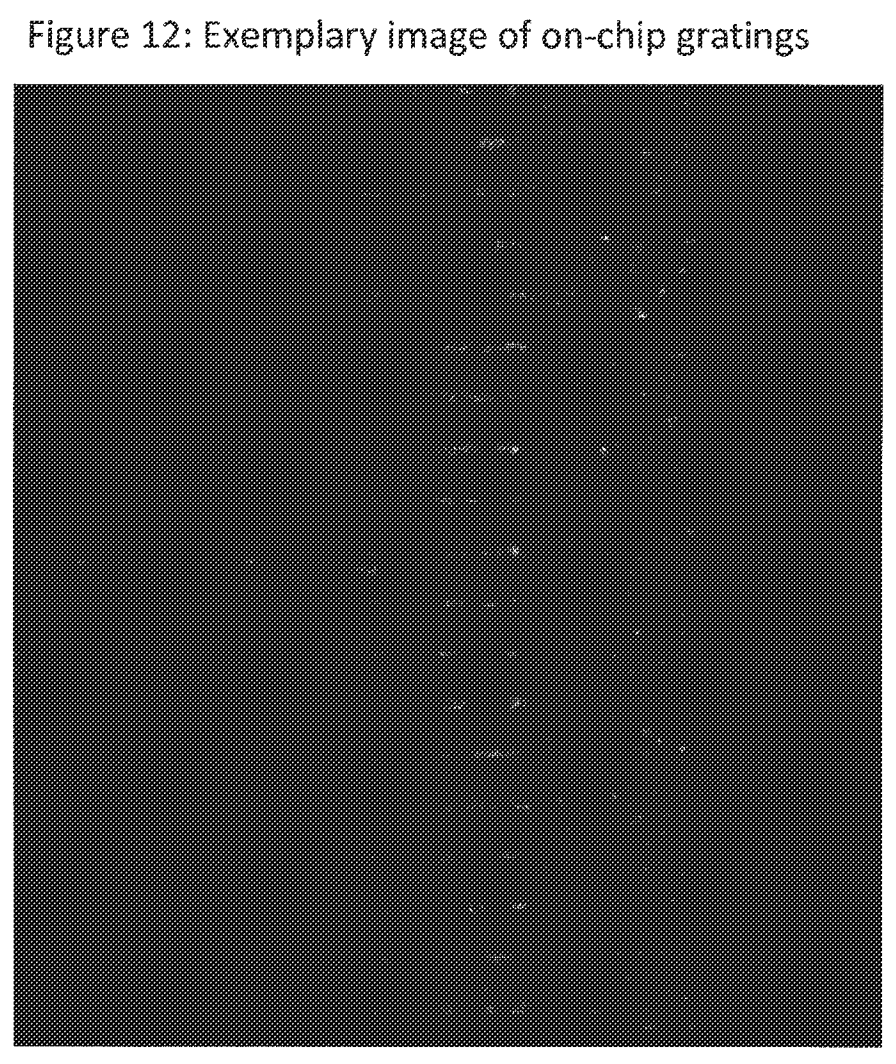

The second of the two collected signals is the "retro" signal which is collected by the photodetector 104 in the fiber optical system 100 and is used during registration. This signal can construct a picture of the chip that has the retroreflective gratings present. The sensor signal collected at the detector 211 is spatially filtered twice, first by the relative positioning of the objective lens 205 and the chip 206 to minimize specular reflection from the chip 205 and second by the spatial filter 209, so that only the sensors show up. The retro signal collected by the detector 104 is unmodified and will show all reflections off the chip surface, an example of which is shown in FIG. 12. The retroreflective grating features are designed to make a much brighter reflection than the rest of the chip surface and therefore stand out on the retro signal in much the same way that the sensors show up on the sensor signal. The physical dimensions of the retroreflective gratings and the angle of the light that is interrogating the chip surface is critical in illumination of the retroreflective grating structures. While the focused beam is rastered over the chip surface, the retro signal is synchronously sampled along with the mirror driver signals and the sensor signal. Like the sensor signal, the retro signal can be reconstructed to draw a picture of the chip surface.

Note that retroreflective grating signals can be uniquely observed using a retro photodetector 104 located on the return path of the fiber system, while the retroreflective signals measured by an optional photodetector in the free space system (located on an alternative arm of the splitter 207) contain both grating coupler and retroreflective grating signals. Alternative embodiments would employ either one, or possibly both, of these signals.

Upon completion of rastering and signal capture, the images generated from the retro and sensor signals can be used in conjunction to uniquely identify each sensor. In the event that the sensor locations and the retroreflective grating signals are generated in different scans, the relative positions are not accurately determined. There is a pixel offset between the two generated images. These pixel offsets translate into time offsets in the rastering ADC sampling domain. Based on the time at which the focused spot crossed over the sensor input, the time at which the spot crossed over the retroreflective grating set can be inferred, and thus the retroreflective grating set associated with each sensor can be determined.

The preferred embodiment is to sample both the retroreflective signal and the grating coupler signal simultaneously, thus avoiding the pixel alignment issue.

Once the pixels of the retroreflective grating set have been calculated, they can then be digitally processed and translated into a usable number (see FIG. 13). In this example of a coding scheme, the bright spots of the retroreflective grating set are considered binary "1"s and the dark spots of the retroreflective grating set are considered "0"s. When sequentially combined, these 1s and 0s make up and N length binary number which uniquely identifies each sensor. The logic threshold of the binary number is dynamically calculated for each retroreflective grating set based on the collected signals' strength and noise level for that particular retroreflective grating set. Error correction is applied to ensure that the ID of each sensor is accurately determined. Error correction is applied by ensuring that the spacing of any sensor pair is a discrete multiple of the known distance between any adjacent sensor pair. For any adjacent or non-adjacent sensor pair IDs, the absolute difference in IDs is equal to the distance between the two sensors divided by the known distance of an adjacent sensor pair. The prior criteria is applied to all sensors found during registration to verify the sensor IDs.

If all sensor IDs have been found to be valid, the sensor locations and their IDs can be used to conduct measurements of the sensors on the chip. The locations of the sensors are used in the free space interrogation phase of instrument execution.

Free space interrogation of the sensors on a chip is achieved by steering the focused spot onto the input grating coupler of a particular sensor and then sweeping the wavelength of the light while the spot is fixed on the input grating coupler of the sensor. The spot is steered with an automated (software controlled) 2-axis mirror. During the registration phase, voltages used for steering the mirror onto each sensor are found and stored in memory. Each sensor input has its own 2D coordinate on the chip surface and is interrogated individually in time and space.

During a measurement, the sensors are interrogated one after the other in round-robin fashion and the sequence is repeated. In some implementations, all physical components involved in the interrogation can be synchronized with a single digital trigger signal. The mirror is moved on the falling edge of the trigger signal and allowed to settle before the next rising edge of the trigger signal. Upon reception of the rising edge of the trigger signal, the tunable laser will start its wavelength scan. The wavelength scan is the primary point of the sensor interrogation. Once the tunable laser has completed its wavelength scan, the trigger signal is toggled low and the mirror is triggered to move to the next sensor.

Figure 14:
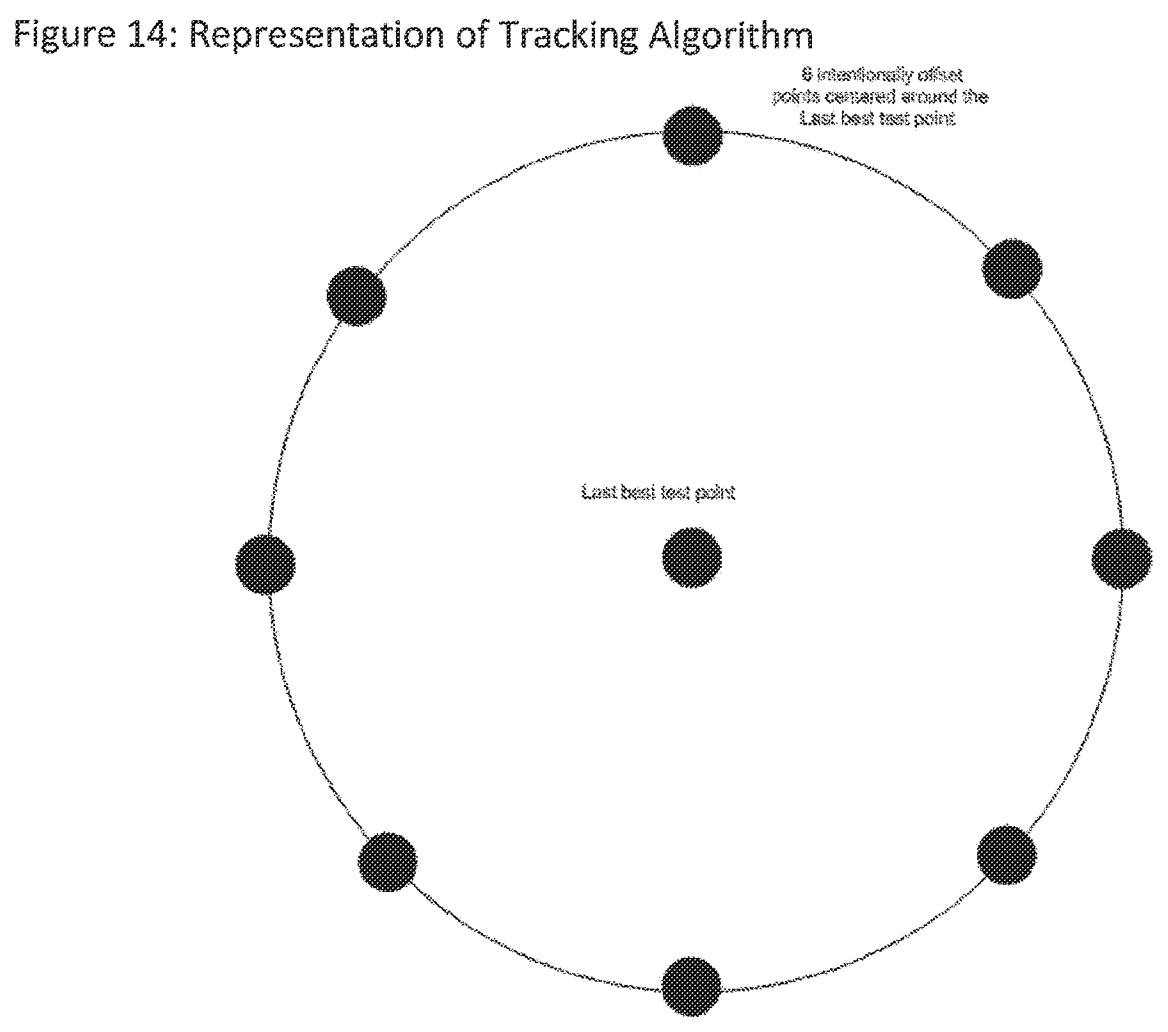

Due to thermal and other effects of the optical interrogator and its internal components, the locations of the sensors may drift over time. This can be countered through the use of a "tracking algorithm" in a calibration process illustrated in FIG. 14. When the spot is not perfectly centered on the sensor input grating coupler, the power detected on the sensor output grating coupler degrades. This can be a problem if feedback is not used to keep the spot aligned with the sensor input grating coupler for long periods of time. The mirror voltages that are used to move the focused spot on the sensor can be purposefully modified as a means of tracking any drift in the system. By taking a mirror coordinate and drawing a very small circle around it and taking discrete points on that circle, new mirror coordinates for subsequent interrogations can be created. These points which tend to deviate slightly from the original point can be used to find which direction is the best for the spot to be steered. After interrogating the same sensor with the new coordinates and recording input coupling efficiency for each spot, a new best coordinate can be chosen. This new coordinate can be used as the centroid of the next set of radial test points. This process of seeking, moving, and following the drift can be used to keep the instrument interrogating the sensors via free space interrogation.

The optical interrogator can be configured to incorporate two software controlled beam steering mirrors 203 and 204 as shown in the example in FIG. 1. The primary function of mirror A (203) is to control the chief ray (aka incidence angle) of the steered beam to the chip surface. The role of mirror B (204) is to control the position of the beam on the chip surface. Mirror B (204) will change incident angle of the beam but to a much lesser degree than mirror A (203). By calibrating the X and Y command voltages for mirror A (203), the coupling efficiency during an experiment can be at its maximum. This results in higher signal to noise levels.

Calibration of the X and Y axis command voltages for mirror B can be achieved by iteratively looping through an NxN set of X and Y axis command voltages for the mirror A. At each iteration mirror B rasters the chip surface and the coupling efficiency profile for all sensors is collected. A 2 dimensional search is completed and the results can be automatically interpreted as to which X,Y pair of mirror A voltages yielded the greatest coupling efficiency. This X,Y mirror A command voltage pair will be used to set the chief ray during experiment phase of instrument use. The values will be stored in a non-volatile memory and loaded into volatile memory each time the instrument is powered on. Mirror A will be commanded to the calibrated voltages during power up initialization and held at that position at all times while the instrument is powered on. The mirror can relax to its nominal position when the instrument is not in use.

An alternative embodiment is to construct the optical interrogation system with sufficient mechanical tolerances to ensure attainment of the appropriate chief-ray. In this scenario, mirror A can be replaced with a fixed mirror, leaving only mirror B as a tunable element.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Only a few examples and implementations are disclosed. Variations, modifications and enhancements to the described examples and implementations and other implementations may be made based on what is disclosed.

What is claimed is:

1. A biosensing system comprising:
a light source configured to generate input light comprising a range of wavelengths;
a beam splitter configured to divide the input light into a first portion and a second portion;
a resonant optical biosensor configured to receive the first portion of the input light and to output a first transmission spectrum of light that comprises a resonance within the range of wavelengths, the resonance corresponding to a wavelength that depends on the presence of an analyte at the resonant optical biosensor;
a first detector configured to detect the first transmission spectrum output from the resonant optical biosensor;
a wavelength referencing device configured to receive the second portion of the input light and to output a second transmission spectrum of light that comprises plurality of resonances within the range of wavelengths;
a second detector configured to detect the second transmission spectrum output from the wavelength referencing device; and
a processor configured to:
analyze the first and second transmission spectra and to determine the wavelength corresponding to the resonance of the first transmission spectrum of light output from the resonant optical biosensor based at least in part on the plurality of resonances in the second transmission spectrum output from the wavelength referencing device;
identify a first resonance in the second transmission spectrum at a wavelength less than a wavelength of the resonance in the first transmission spectrum;
identify a second resonance in the second transmission spectrum at a wavelength greater than that of the resonance in the first transmission spectrum; and
determine the wavelength corresponding to the resonance of the first transmission spectrum of light output from the resonant optical biosensor, at least in part, by determining a position of the resonance of the first transmission spectrum with respect to the first and second resonances of the second transmission spectrum.

2. The biosensing system of claim 1, wherein the light source is a wavelength tunable light source.

3. The biosensing system of claim 2, wherein the light source is configured to sweep the wavelength of the input light through the range of wavelengths over time.

4. The biosensing system of claim 1, wherein:
the first transmission spectrum comprises a plurality of resonances of the resonant optical biosensor, the plurality of resonances in the first transmission spectrum indicating the presence of the analyte at the resonant optical biosensor, and the plurality of resonances and having a first free spectral range wavelength spacing therebetween;
the plurality of resonances in the second transmission spectrum have a second free spectral range wavelength spacing therebetween; and
the first free spectral range is larger than the second free spectral range and wherein the processor is further configured to:
for each of the plurality of resonances in the first transmission spectrum:
identify a first resonance in the second transmission spectrum at a wavelength less than a wavelength of the resonance in the first transmission spectrum;
identify a second resonance in the second transmission spectrum at a wavelength greater than that of the resonance in the first transmission spectrum; and
determine the wavelength corresponding to the resonance of the first transmission spectrum of light output from the resonant optical biosensor, at least in part, by determining a position of the resonance of the first transmission spectrum with respect to the first and second resonances of the second transmission spectrum.

5. The biosensing system of claim 4, wherein the processor is further configured to:
for each of the plurality of resonances in the first transmission spectrum, identify a respective first resonance in the second transmission spectrum at a wavelength less than that of the respective resonance in the first transmission spectrum;
for each of the plurality of resonances in the first transmission spectrum, identify a respective second resonance in the second transmission spectrum at a wavelength greater than that of the respective resonance in the first transmission spectrum; and
determine the wavelength corresponding to the resonance of the resonant optical biosensor at least in part by, for each of the plurality of resonances in the first transmission spectrum, determining a position of the respective resonance of the first transmission spectrum with respect to the respective first and second resonances of the second transmission spectrum.

6. The biosensing system of claim 1, wherein the resonant optical biosensor comprises a ring resonator and an adjacent waveguide.

7. The biosensing system of claim 1, wherein the wavelength referencing device comprises an etalon.

8. The biosensing system of claim 1, wherein the system is configured to provide the first portion of the input light to the resonant optical biosensor and to provide the second portion of the input light to the wavelength referencing device simultaneously.

9. The biosensing system of claim 8, wherein the system is configured to obtain samples from the first transmission spectrum and the second transmission spectrum simultaneously.

10. A method comprising:
generating input light comprising a range of wavelengths;

dividing the input light into a first portion and a second portion;

providing the first portion of the input light to a resonant optical biosensor;

receiving, in response to the provision of the first portion of the input light to the resonant optical biosensor, a first transmission spectrum of light that comprises a resonance within the range of wavelengths, the resonance corresponding to a wavelength that depends on the presence of an analyte at the resonant optical biosensor;

detecting, with a first detector, the first transmission spectrum received from the resonant optical biosensor;

providing the second portion of the input light to a wavelength referencing device;

detecting, with a second detector, a second transmission spectrum of light that comprises a plurality of resonances within the range of wavelengths, wherein the second transmission spectrum is output from the wavelength referencing device in response to the provision of the second portion of the input light to the wavelength referencing device;

analyzing the first and second transmission spectra and to determine a wavelength corresponding to the resonance of the first transmission spectrum based at least in part on the plurality of resonances in the second transmission spectrum output from the wavelength referencing device;

identifying a first resonance in the second transmission spectrum at a wavelength less than a wavelength of the resonance in the first transmission spectrum;

identifying a second resonance in the second transmission spectrum at a wavelength greater than that of the resonance in the first transmission spectrum; and determining the wavelength corresponding to the resonance of the first transmission spectrum of light output from the resonant optical biosensor, at least in part, by determining a position of the resonance of the first transmission spectrum with respect to the first and second resonances of the second transmission spectrum.

11. The method of claim 10, wherein generating input light comprising a range of wavelengths includes sweeping a wavelength of the input light through the range of wavelengths over time.

12. The method of claim 10, wherein:

the first transmission spectrum comprises a plurality of resonances of the resonant optical biosensor, the plurality of resonances in the first transmission spectrum indicating the presence of the analyte at the resonant optical biosensor, and the plurality of resonances having a first free spectral range wavelength spacing therebetween;

the plurality of resonances in the second transmission spectrum have a second free spectral range wavelength spacing therebetween;

the first free spectral range is larger than the second free spectral range, and the method further comprising:

for each of the plurality of resonances in the first transmission spectrum:

identifying a first resonance in the second transmission spectrum at a wavelength less than a wavelength of the resonance in the first transmission spectrum;

identifying a second resonance in the second transmission spectrum at a wavelength greater than that of the resonance in the first transmission spectrum; and determining the wavelength corresponding to the resonance of the first transmission spectrum of light output from the resonant optical biosensor, at least in part, by determining a position of the resonance of the first transmission spectrum with respect to the first and second resonances of the second transmission spectrum.

13. The method of claim 12, further comprising:

for each of the plurality of resonances in the first transmission spectrum, identifying a respective first resonance in the second transmission spectrum at a wavelength less than that of the respective resonance in the first transmission spectrum;

for each of the plurality of resonances in the first transmission spectrum, identifying a respective second resonance in the second transmission spectrum at a wavelength greater than that of the respective resonance in the first transmission spectrum; and determining the wavelength corresponding to the resonance of the resonant optical biosensor at least in part by, for each of the plurality of resonances in the first transmission spectrum, determining a position of the respective resonance of the first transmission spectrum with respect to the respective first and second resonances of the second transmission spectrum.

14. The method of claim 10, wherein the resonant optical biosensor comprises a ring resonator and an adjacent waveguide.

15. The method of claim 10, wherein the wavelength referencing device comprises an etalon.

16. The method of claim 10, wherein providing the first portion of the input light to a resonant optical biosensor and providing the second portion of the input light to a wavelength referencing device occurs simultaneously.

17. The method of claim 10, wherein detecting, with the first detector, the first transmission spectrum received from the resonant optical biosensor and detecting, with the second detector, a second transmission spectrum of light that comprises a plurality of resonances within the range of wavelengths occurs simultaneously.

* * * * *